United States Patent
Yoon

[11] Patent Number: 6,126,665
[45] Date of Patent: Oct. 3, 2000

[54] SURGICAL INSTRUMENT WITH ARCUATELY MOVABLE OFFSET END EFFECTORS AND METHOD OF USING THE SAME

[76] Inventor: InBae Yoon, 2101 Highland Ridge Dr., Phoenix, Md. 21131

[21] Appl. No.: 08/899,710

[22] Filed: Jul. 23, 1997

Related U.S. Application Data

[63] Continuation-in-part of application No. 08/847,254, May 1, 1997, Pat. No. 6,004,332.

[51] Int. Cl.[7] .................................................. A61B 17/04
[52] U.S. Cl. ........................................ 606/144; 606/144
[58] Field of Search .................................. 606/139, 144, 606/148, 151, 223, 224

[56] References Cited

U.S. PATENT DOCUMENTS

| | | |
|---|---|---|
| 919,138 | 4/1909 | Drake et al. . |
| 1,037,864 | 9/1912 | Carlson et al. . |
| 1,449,087 | 3/1923 | Bugbee . |
| 1,822,330 | 9/1931 | Ainslie . |
| 2,213,830 | 9/1940 | Anastasi . |
| 2,646,045 | 7/1953 | Priestley . |
| 2,959,172 | 11/1960 | Held . |
| 3,090,386 | 5/1963 | Curtis . |
| 3,139,089 | 6/1964 | Schwerin . |
| 3,349,772 | 10/1967 | Rygg . |
| 3,470,875 | 10/1969 | Johnson . |
| 3,842,840 | 10/1974 | Schweizer . |
| 3,946,740 | 3/1976 | Bassett . |
| 4,109,658 | 8/1978 | Hughes . |
| 4,164,225 | 8/1979 | Johnson et al. . |
| 4,440,171 | 4/1984 | Nomoto et al. . |
| 4,557,265 | 12/1985 | Andersson . |
| 4,621,640 | 11/1986 | Mulhollan et al. . |
| 4,635,638 | 1/1987 | Weintraub et al. . |
| 4,935,027 | 6/1990 | Yoon . |
| 5,037,433 | 8/1991 | Wilk et al. . |
| 5,100,421 | 3/1992 | Christoudias . |
| 5,147,373 | 9/1992 | Ferzli . |
| 5,181,919 | 1/1993 | Bergman et al. . |
| 5,211,650 | 5/1993 | Noda . |
| 5,222,508 | 6/1993 | Contarini . |
| 5,234,443 | 8/1993 | Phan et al. . |
| 5,244,948 | 9/1993 | Mulhaupt et al. . |
| 5,261,917 | 11/1993 | Hasson et al. . |
| 5,281,238 | 1/1994 | Chin et al. . |
| 5,304,185 | 4/1994 | Taylor . |
| 5,308,353 | 5/1994 | Beurrier . |
| 5,320,632 | 6/1994 | Heidmueller . |
| 5,336,230 | 8/1994 | Leichtling et al. . |
| 5,336,231 | 8/1994 | Adair . |
| 5,356,424 | 10/1994 | Buzerak et al. . |
| 5,364,408 | 11/1994 | Gordon . |
| 5,364,409 | 11/1994 | Kuwabara et al. . |
| 5,374,275 | 12/1994 | Bradley et al. . |
| 5,376,096 | 12/1994 | Foster . |
| 5,389,098 | 2/1995 | Tsuruta et al. . |
| 5,389,103 | 2/1995 | Melzer et al. . |
| 5,395,367 | 3/1995 | Wilk . |
| 5,397,325 | 3/1995 | Della Badia et al. . |
| 5,403,328 | 4/1995 | Shallman . |
| 5,403,329 | 4/1995 | Hinchcliffe . |
| 5,437,681 | 8/1995 | Meade et al. . |
| 5,454,823 | 10/1995 | Richardson et al. . |
| 5,462,561 | 10/1995 | Voda . |
| 5,462,562 | 10/1995 | Elkus . |

(List continued on next page.)

*Primary Examiner*—Michael Buiz
*Assistant Examiner*—Anthony King
*Attorney, Agent, or Firm*—Blank Rome Comisky & McCauley LLP

[57] ABSTRACT

An instrument for manipulating anatomical tissue and a method of using the instrument. A barrel has two drivers therein which can be manipulated from a proximal end of the barrel. The end effector of each driver are offset from a shaft by a transverse arm. In an insertion position, the end effectors are confined within the diametrical dimension of the barrel at a distal end thereof. After insertion, the end effectors can be manipulated by rotationally or arcuately moving the shafts to extend beyond the diametrical dimension of the barrel to provide a large working span in which a tissue procedure can be accomplished.

36 Claims, 14 Drawing Sheets

U.S. PATENT DOCUMENTS

| | | |
|---|---|---|
| 5,468,251 | 11/1995 | Buelna . |
| 5,470,338 | 11/1995 | Whitfield et al. . |
| 5,474,057 | 12/1995 | Makower et al. . |
| 5,474,568 | 12/1995 | Scott . |
| 5,477,794 | 12/1995 | Klundt . |
| 5,478,344 | 12/1995 | Stone et al. . |
| 5,478,345 | 12/1995 | Stone et al. . |
| 5,480,406 | 1/1996 | Nolan et al. . |
| 5,496,334 | 3/1996 | Klundt et al. . |
| 5,503,634 | 4/1996 | Christy . |
| 5,520,703 | 5/1996 | Essig et al. . |
| 5,540,704 | 7/1996 | Gordon et al. . |
| 5,540,705 | 7/1996 | Meade et al. . |
| 5,545,148 | 8/1996 | Wurster . |
| 5,562,640 | 10/1996 | McCabe et al. . |
| 5,562,685 | 10/1996 | Mollenauer et al. . |
| 5,562,686 | 10/1996 | Sauer et al. . |
| 5,562,703 | 10/1996 | Desai . |
| 5,569,164 | 10/1996 | Lurz . |
| 5,569,269 | 10/1996 | Hart et al. . |
| 5,569,270 | 10/1996 | Weng . |
| 5,573,542 | 11/1996 | Stevens . |
| 5,578,048 | 11/1996 | Pasqualucci et al. . |
| 5,582,617 | 12/1996 | Klieman et al. . |
| 5,591,181 | 1/1997 | Stone et al. . |
| 5,601,575 | 2/1997 | Measamer et al. . |
| 5,607,435 | 3/1997 | Sachdeva et al. . |
| 5,609,601 | 3/1997 | Kolesa et al. . |
| 5,626,588 | 5/1997 | Sauer et al. . |
| 5,632,751 | 5/1997 | Piraka . |
| 5,632,752 | 5/1997 | Buelna . |
| 5,643,292 | 7/1997 | Hart . |
| 5,662,663 | 9/1997 | Shallman . |
| 5,674,230 | 10/1997 | Tovey et al. . |
| 5,707,379 | 1/1998 | Fleenor et al. . |
| 5,709,693 | 1/1998 | Taylor . |
| 5,709,694 | 1/1998 | Greenberg et al. . |

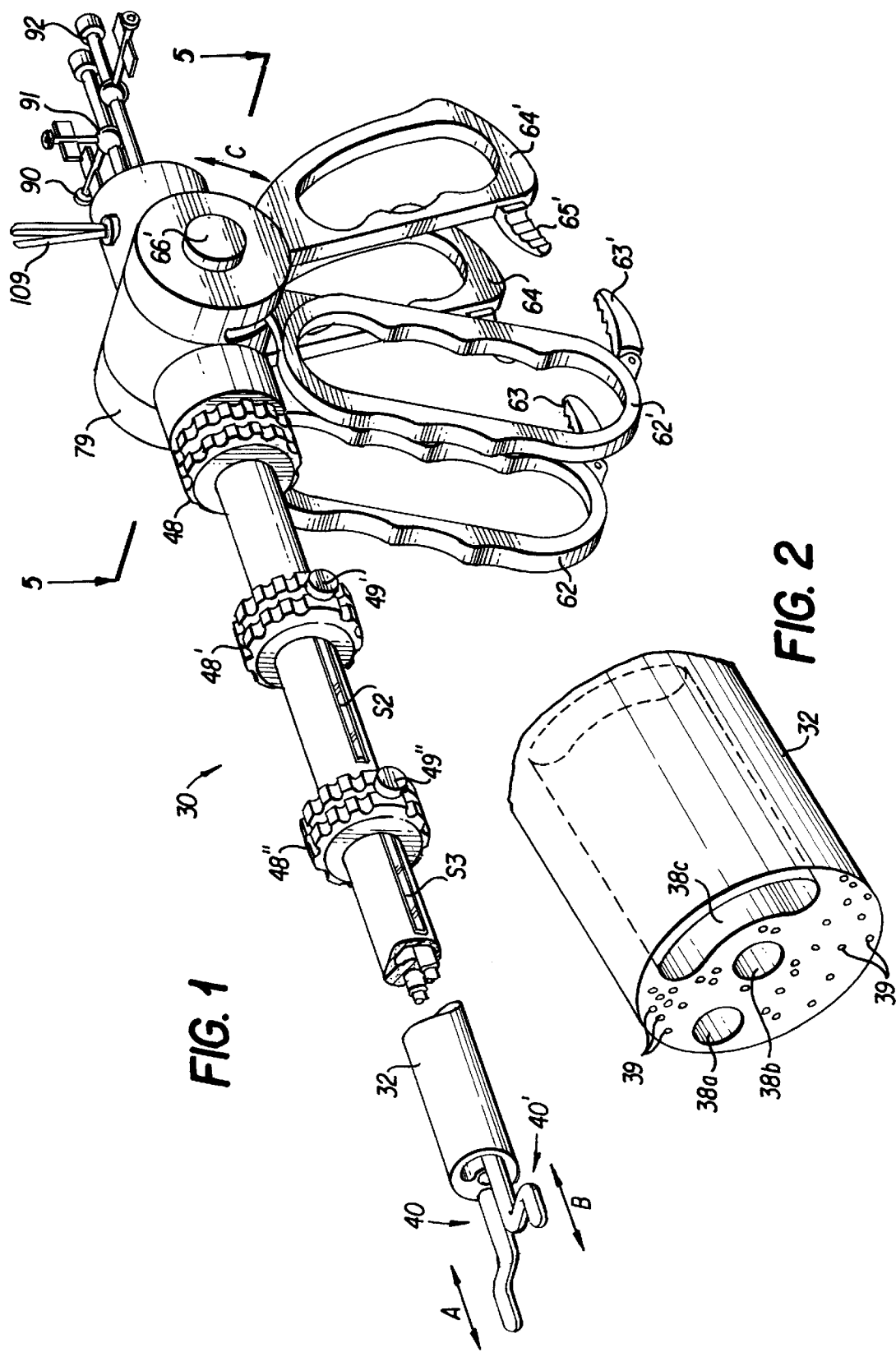

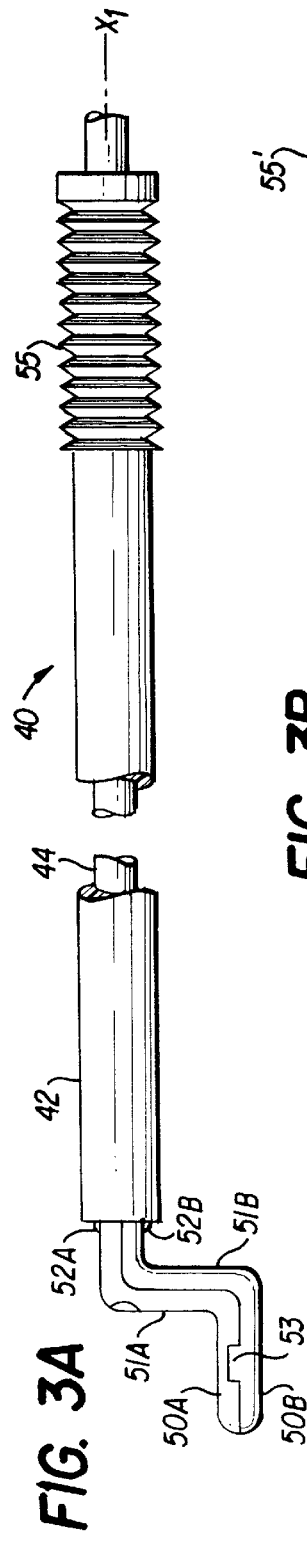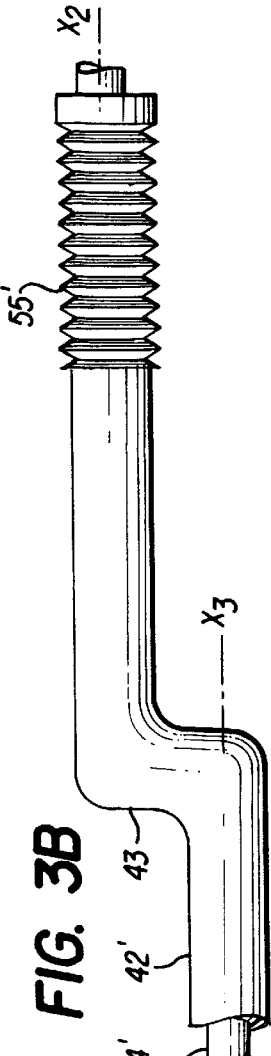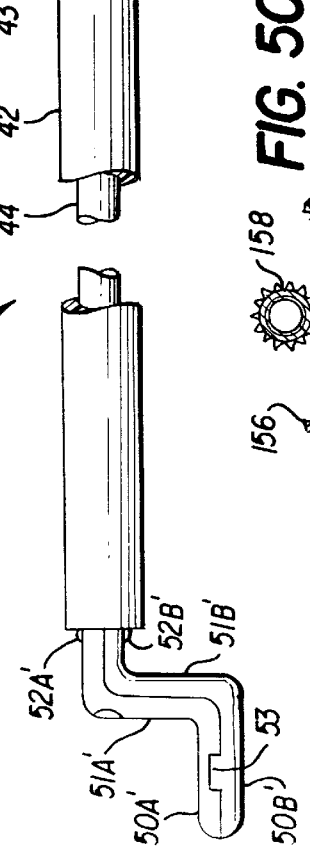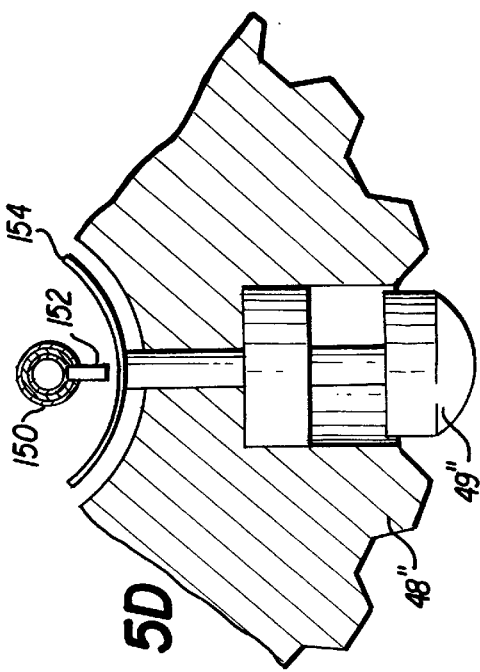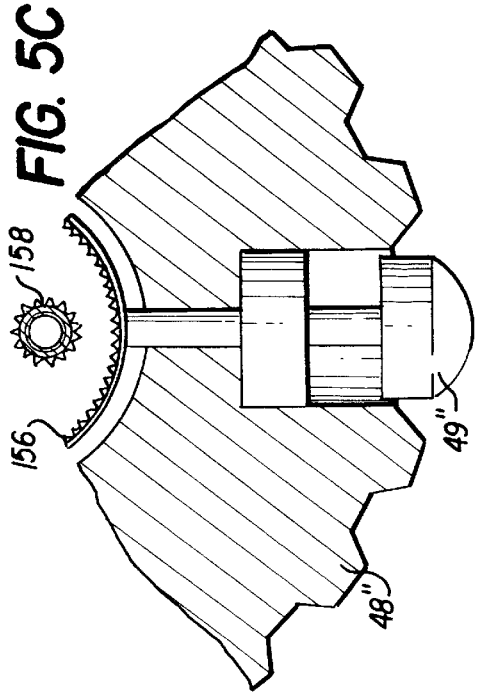
FIG. 3A
FIG. 3B
FIG. 5C
FIG. 5D

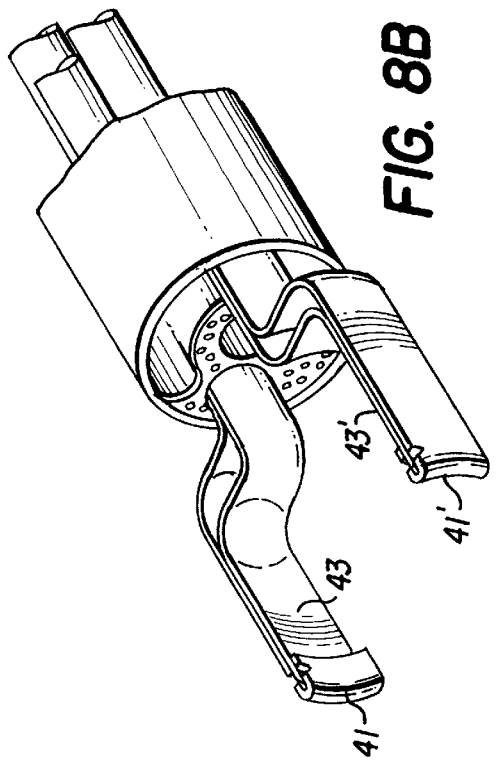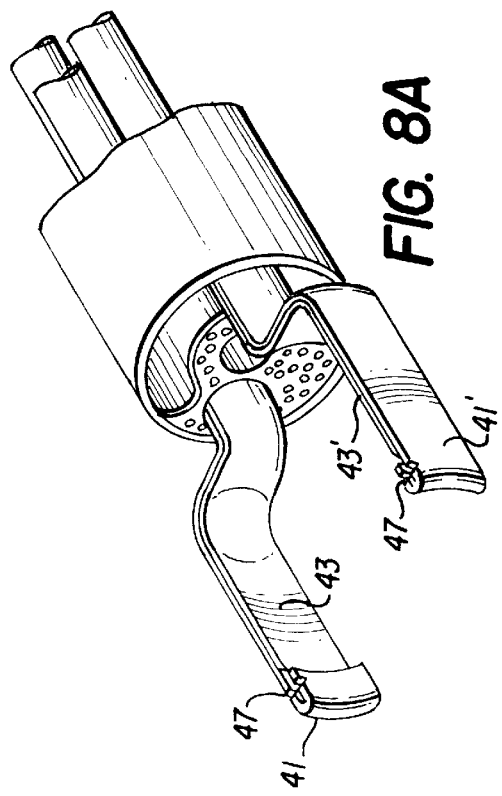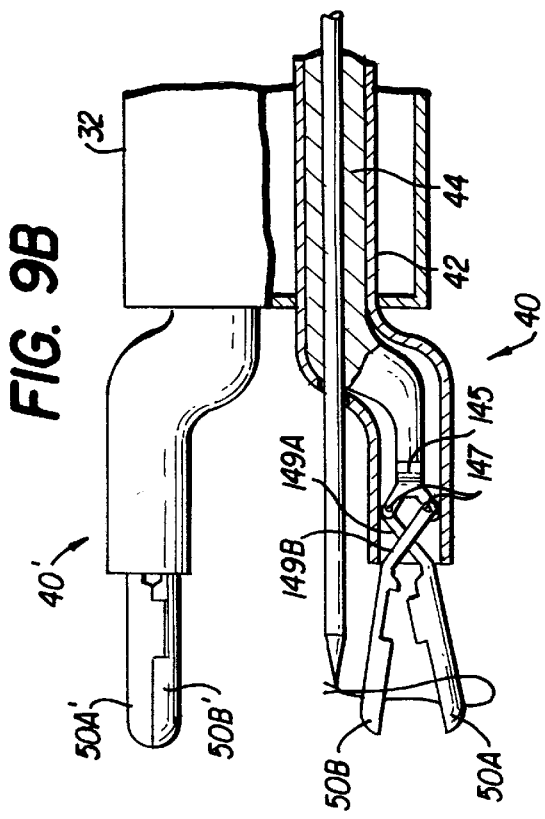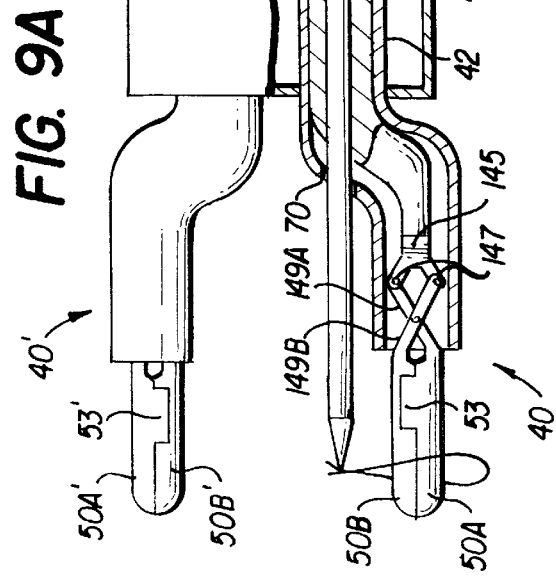

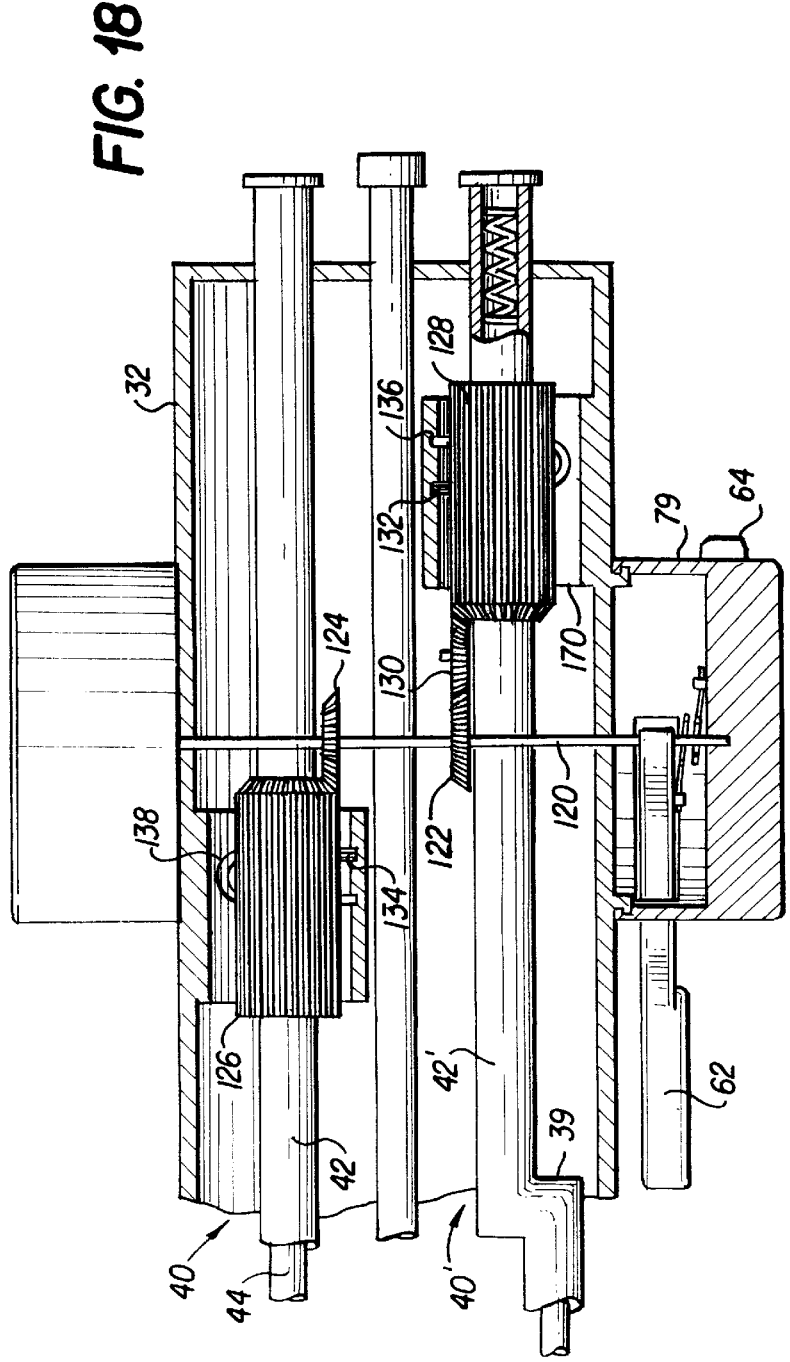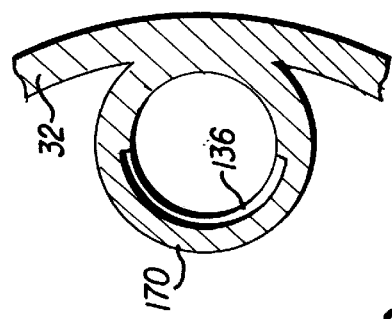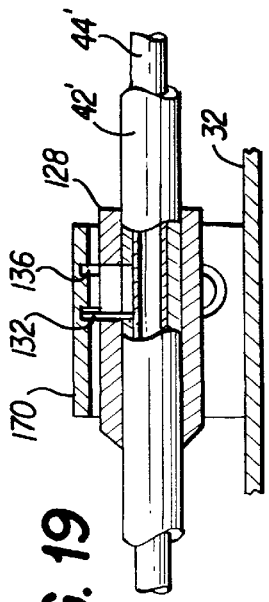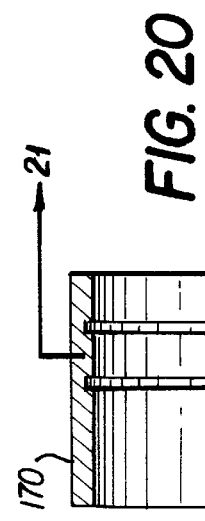

SURGICAL INSTRUMENT WITH ARCUATELY MOVABLE OFFSET END EFFECTORS AND METHOD OF USING THE SAME

RELATED PATENT APPLICATION DATA

This application is a continuation-in-part of applicant's application Ser. No. 08/847,254 filed on May 1, 1997, now U.S. Pat. No. 6,004,332 the disclosure of which is incorporated herein by reference. Also, this application is related to U.S. application Ser. No. 08/847,182, the disclosure of which is also incorporated herein by reference.

BACKGROUND OF THE INVENTION

1. Field of the Invention

The present invention pertains to manipulation of bodily or anatomical tissue and, more particularly, to an apparatus and method for manipulating anatomical tissue during minimally invasive and open surgical procedures.

2. Discussion of the Related Art

It is often desirable to manipulate anatomical tissue using multiple instruments in cooperation with one another. For example, suturing of bodily tissue, that is, the practice of using lengths of suture material to ligate or approximate tissue, is a time consuming part of most surgical procedures including both open surgery and endoscopic or closed surgery. "Open surgery" refers to surgery wherein the surgeon gains access to the surgical site by a relatively large incision and "endoscopic surgery" refers to any minimally invasive surgery wherein the surgeon gains access to the surgical site via one or more portals through which endoscopes may be introduced to view the surgical site and through which instruments, such as forceps, cutters, needle holders and the like, are introduced to the surgical site.

In the past, suturing has been accomplished with the use of a sharp suture needle carrying a length of suture material, the suture needle being caused to penetrate and pass through the tissue pulling the suture material through the tissue. Once the suture material has been pulled through the tissue, the surgeon ties a knot in the suture material. The knotting procedure allows the surgeon to adjust the tension on the suture material to accommodate the particular tissue being sutured and to control approximation, occlusion, attachment or other conditions of the tissue.

The process of tissue penetration and knotting of the suture material can be time consuming and tedious work, particularly when performed in connection with microsurgery and endoscopic surgery and can unduly prolong the duration of surgery and therefore the period in which the patient is under anesthesia. Nevertheless, endoscopic surgery is preferred over open surgery due to the greatly reduced trauma and wound healing time for the patient and due to cost savings associated with shorter hospital stays and performing surgery in non-hospital or out-patient surgery sites. Accordingly, there has been much effort to develop endoscopic techniques for facilitating the suturing normally performed by use of a suture needle and a length of suture material. Alternative techniques proposed have included electrical coagulation, mechanical devices such as clips, clamps and staples, and lasers. However, no alternative technique has yet been well accepted by surgeons to produce the results obtained by suturing and knotting. Thus, there is a great need for suturing techniques useful in endoscopic surgery to permit surgeons to suture anatomical tissue using suture needles and lengths of suture material in a time efficient, consistent and precise manner.

The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, or instruments having scissors, forceps, needle holders and the like (known generally as "end effectors") into the anatomical cavity.

Suturing, for example, is typically performed with a needle holding instrument, or needle holder, having a pair of jaws adapted to hold the body of a suture needle. The jaws of the needle holding instrument are inserted through the portal sleeve and are positioned at the operative site by manipulation of a handle at the proximal end of the instrument outside the body. With a suture needle held between the jaws of the needle holding instrument, the handle is manipulated to cause a tip of the needle to be pushed through the tissue being sutured. Once the tip of the suture needle has been pushed through the tissue, the jaws of the needle holding instrument must be opened to release the suture needle so that the tip of the needle can be grasped and pulled through the tissue therewith, or, after opening the jaws, a second needle holding instrument must be introduced at the operative site through another portal to grasp the tip of the suture needle after it has emerged from the tissue being sutured.

The former technique requires difficult manipulation and further adjustment of the suture needle within the jaws of the needle holder before another stitch can be made. While use of a second needle holding instrument for pulling the needle through the anatomical tissue allows the first needle holding instrument to grasp the body of the suture needle in the manner required to make additional stitches, a second puncture site is required to permit insertion of the second instrument. It is generally desirable to minimize the number of puncture sites created for performing a particular endoscopic procedure.

Of course, it is also generally desirable to minimize the size of each puncture site. Further, in order to permit a wide range of tissue sizes to be sutured, it is desirable to provide a wide range of relative movement between the two needle holder instruments, i.e. a large working span.

These objectives, minimal number punctures, small size of punctures, and a wide range of relative movement, are seemingly contradictory. Conventional devices have not achieved the above-noted objectives in a satisfactory manner. The need for a large working span is not limited to suturing procedures. In fact, instruments having a large working span are desirable in all types of tissue manipulation such as lysis of adhesion, pickup and cutting, pickup and clipping, and other procedures. Further, it is desirable to use similar instruments and controls in both open surgery and minimally invasive surgery for consistency in training.

SUMMARY OF THE INVENTION

Accordingly, it is a primary object of the present invention to overcome the above-mentioned disadvantages of the prior art and to improve surgical instruments and methods of manipulating anatomical tissue.

Yet another object of the present invention is to minimize the number of puncture sites required for suturing anatomical tissue, or otherwise manipulating the tissue, in an endoscopic procedure by inserting a pair of needle holders, or other end effectors, through a single puncture site with an instrument that is operable to move the end effectors relative to one another in a cooperative manner to suture anatomical tissue.

It is a further object of the present invention to permit an instrument having multiple end effectors that are movable relative to one another to be introduced through a single portal in an endoscopic procedure without having to withdraw the suturing instrument from the portal.

It is another object of the invention to permit an endoscopic device to have a large working span and a small insertion diameter and to replicate the natural motion of needle passage through tissue.

Finally, it is an object of the invention to control an endoscopic or open surgical suturing procedure with standard proximal end controls.

The present invention allows manipulation of anatomical tissue to be accomplished in a time efficient, consistent and precise manner. Also, suturing can be accomplished using standard suture needles and filamentous suture materials without the need for additional instruments at the operative site.

A first aspect of the present invention is generally characterized in an instrument for suturing anatomical tissue with a suture needle including a barrel, a needle driver having a shaft that is mounted in the barrel for rotation about a first axis, and a needle catcher having a shaft that is mounted in the barrel for rotation about a second axis and for arcuate movement about a third axis. The needle driver and the needle catcher each include needle holding members offset from the first and second axes respectively and selectively operable to grasp and release the suture needle. The needle holding members are coupled to the shafts by arms or connecting portions extending from a distal end of the shafts. When the needle holding members of the needle driver are operated to grasp the suture needle, the needle driver can be rotated to drive the suture needle through anatomical tissue positioned between the needle driver and the needle catcher, and when the needle holding members of the needle catcher are operated to grasp the suture needle, the needle holding members of the needle driver can be operated to release the suture needle, thereby allowing the needle catcher to be rotated and/or moved arcuately to pull the suture material through the anatomical tissue. During insertion into an anatomical cavity through a portal or the like, the needle holding members are contained within a diametrical dimension of the barrel. However during suturing, the needle holding members can extend beyond this dimension due to the offset configuration.

Another aspect of the present invention is generally characterized in a method of suturing anatomical tissue using a length of suture material attached to a suture needle. The method includes the steps of grasping the suture needle with offset needle holding members of a needle driver, positioning the anatomical tissue between a tip of the suture needle and a needle catcher, rotating the needle driver in a first direction to cause the tip of the needle to penetrate the anatomical tissue, receiving the tip of the suture needle in offset needle holding members of the needle catcher, grasping the suture needle with the needle catcher, releasing the suture needle from the needle driver, and rotating and/or arcuately moving the needle catcher to pull the needle and the suture material through the anatomical tissue.

In another aspect of the invention, the end effectors of the instrument are forceps jaws, clip applicators, dissecting tools, staplers, cautery electrodes, or the like and are used in a cooperating manner to manipulate tissue during a procedure.

Other objects and advantages of the present invention will become apparent from the following description of the preferred embodiments taken in conjunction with the accompanying drawings, wherein like parts in each of the several figures are identified by the same reference numerals.

BRIEF DESCRIPTION OF THE DRAWINGS

The invention will be described through preferred embodiments illustrated in the following drawing in which:

FIG. 1 is a perspective view of a first preferred embodiment of the invention;

FIG. 2 is a perspective view of a distal end of the barrel of the first preferred embodiment with the drivers removed for clarity;

FIG. 3A is a side view of one of the drivers of the first preferred embodiment;

FIG. 3B is a side view of the other driver of the first preferred embodiment;

FIG. 5C is a partial sectional view taken along line 5C—5C in FIG. 5B;

FIG. 5D is a partial sectional view taken along line 5D—5D in FIG. 5B;

FIG. 8A illustrates a distal end of a fourth preferred embodiment of the invention with the needle holders in an open position;

FIG. 8B illustrates a distal end of the fourth preferred embodiment of the invention with the needle holders in a closed position;

FIG. 9A illustrates a distal end of a fifth preferred embodiment of the invention with jaws in the closed position, in partial section;

FIG. 9B illustrates a distal end of the fifth preferred embodiment with the jaws in the open position, in partial section;

FIG. 18 illustrates an alternative automatic proximal controls;

FIG. 19 illustrates a portion of the controls of FIG. 18 in detail, in partial section;

FIG. 20 illustrates the cylindrical member of FIG. 18; and

FIG. 21 illustrates the cylindrical member in section taken along line 21—21 of FIG. 20.

DETAILED DESCRIPTION OF THE PREFERRED EMBODIMENTS

Figure 4A:
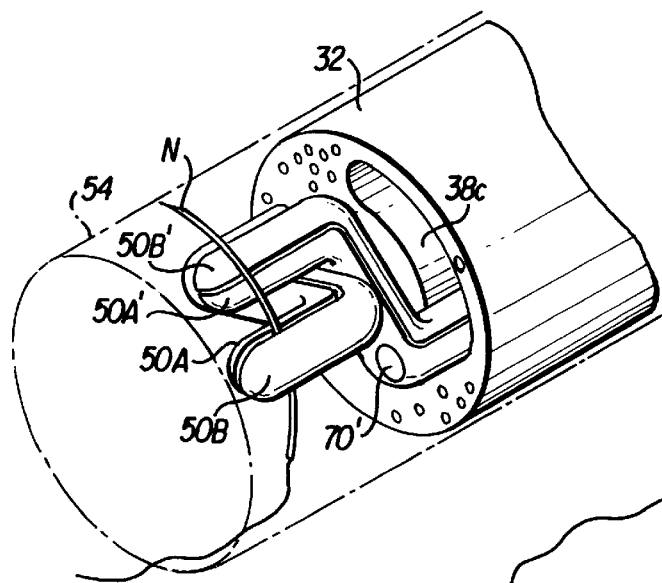
FIG. 4A illustrates the distal end of the first preferred embodiment in a parked or insertion position.

The instrument of the present invention can be utilized to manipulate any type of anatomical tissue in any type of anatomical cavity. Accordingly, while the instrument is described hereinafter for use with a portal sleeve in endoscopic procedures, such as laparoscopy, the instrument can be used in open surgery and with catheters and other small and large diameter tubular or hollow cylindrical members providing access to small cavities, such as veins and arteries, as well as large cavities, such as the abdomen. Also, the first preferred embodiment is described through a suturing procedure. However, the invention can have any end effectors for manipulating tissue in any manner or for accomplishing any desired procedure.

A suturing instrument according to a first preferred embodiment of the present invention is illustrated at 30 in FIG. 1 and includes cylindrical barrel, or outer shaft, 32 which has an elongated passage defined therein, needle driver 40, and needle catcher 40'. Needle driver 40 and needle catcher 40' are substantially contained within cylindrical barrel 32 as is described in detail below. The terms "needle driver" and "needle catcher" are used herein to describe, in terms of their function, elements that may be structurally similar in the preferred embodiment. However, the function of these two elements herein is interchangeable. For example, the functions of the needle driver and needle catcher can be interchanged. Also, these elements are sometimes referred to generically as "needle holders" herein. Also, similar elements having various end effectors, including but not limited to needle holding members, may be referred to as "drivers", "operators", "supports", or "assemblies" herein and are understood to encompass any structure associated with an end effector whether or not the structure actually drives or otherwise imparts function to the end effector. As shown by arrows A and B in FIG. 1, needle driver 40 and needle catcher 40' can be moved, independently of one another, proximally and distally in barrel 32. This movement will be described in detail below.

As shown in FIG. 2 which illustrates a distal end of barrel 32 with needle driver 40 and needle catcher 40' removed, barrel 32 has channel 38a, central channel 38b, and arcuate slot 38c, extending longitudinally therethrough. Slot 38c extends through barrel 32 to a proximal end as illustrated in FIG. 2 by the dotted line and as described in greater detail below. Barrel 32 can have additional channels for receiving one or more additional instruments, or to be used for suction, aspiration, or the like, or barrel 32 can have fewer channels as needed. Optical fibers 39 extend through barrel 32 to transmit light or other energy from a proximal source to the body cavity of a patient. Channels 38a and 38b can be formed by thin wall, tubular sleeves extending longitudinally through barrel 32 or merely by void spaces defined between optical fibers 39. Similarly, slot 38c can be defined by a thin hollow elongated member having the appropriate arcuate cross section or merely by a void space between optical fibers 39. A shaft of needle driver 40 extends through channel 38a and a shaft of needle catcher 40' extends through groove 38c.

FIG. 3A. illustrates needle driver 40 removed from barrel 32 for illustrative purposes. Needle driver 40 includes elongated, tubular outer member 42 and elongated tubular inner member 44 disposed within outer member 42. Outer member 42 and inner member 44 define the shaft that is disposed in channel 38a and is rotatable in barrel 32 about axis $X_1$ which corresponds to the longitudinal axis of outer member 42. Outer member 42 has a proximal end on which collar 55 is disposed. The function of collar 55 is described in detail below.

Figure 4B:
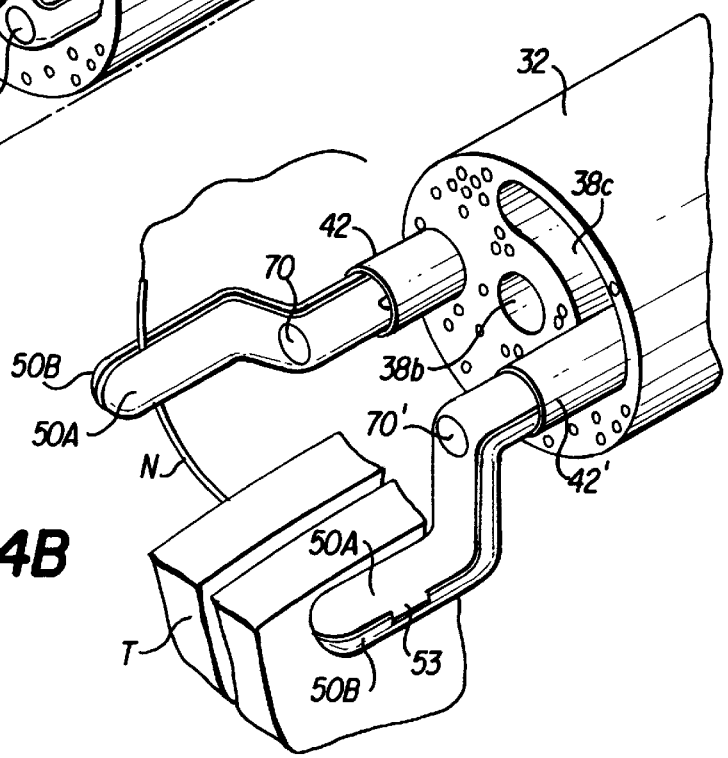
FIG. 4B illustrates a distal end of the first preferred embodiment positioned to drive a suture needle through tissue.

Arms 51A and 51B serve as connecting members between jaw members 50A and 50B and inner member 44 and can be made entirely or partly of resilient, flexible or spring materials, or materials having shape memory. Jaw members 50A and 50B serve as needle holding members and are biased to be normally disposed to an open position wherein the jaw members have a gap defined therebetween. This permits the shank of a suture needle, or any other object, to be placed between jaw members 50A and 50B and to be grasped thereby. Of course, the inner surfaces of jaw members 50A and 50B can be shaped to correspond to the needle shank, or any other appropriate way, to firmly grasp the needle, or the like, when the jaw members 50A and 50B are in a closed position as shown in FIGS. 3, 4A and 4B. Cam surfaces 52A and 52B are formed on arms 51A and 51 B respectively. When outer member 42 is moved distally relative to inner member 44, outer member 42 pushes at least partly over cam surfaces 52A and 52B to push jaw members 50A and 50B towards one another to the closed position.

Needle driver 40 can be designed in various known ways permitting jaw members 50A and 50B to be movable between the closed position and the open position. In this embodiment, the arms, jaw members and inner member are integrally formed. However, the arms can be configured in any manner to serve as a connecting member between the shaft and the jaws which are laterally offset from the shaft. The opening and closing movement of jaw members 50A and 50B of needle driver 40 in the first preferred embodiment is described in detail below.

FIG. 3B illustrates needle catcher 40' removed from barrel 32. Needle catcher 40' includes elongated tubular outer member 42' and elongated tubular inner member 44' disposed within outer member 42'. Outer member 42' and inner member 44' define the shaft that is disposed in slot 38c and is rotatable in barrel 32 about axis $X_2$ and axis $X_3$. Outer member 42' has a proximal end on which collar 55' is disposed. It can be seen that needle catcher 40' is constructed similarly to needle driver 40 in this embodiment. However, inner member 44' and outer member 42' define bent portion 43 at a proximal end of needle catcher 40'. The purpose of bent portion 43 will become apparent below.

Figure 4C:
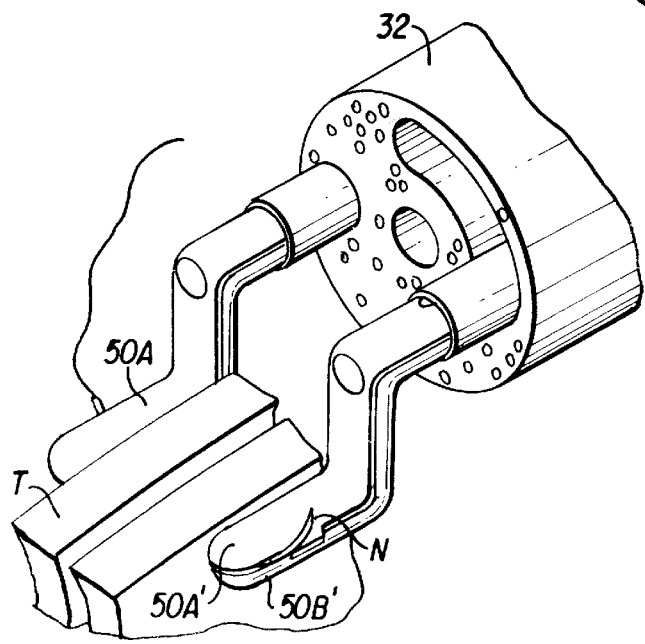
FIG. 4C illustrates a distal end of the first preferred embodiment having driven a suture needle into tissue T.
Figure 4D:
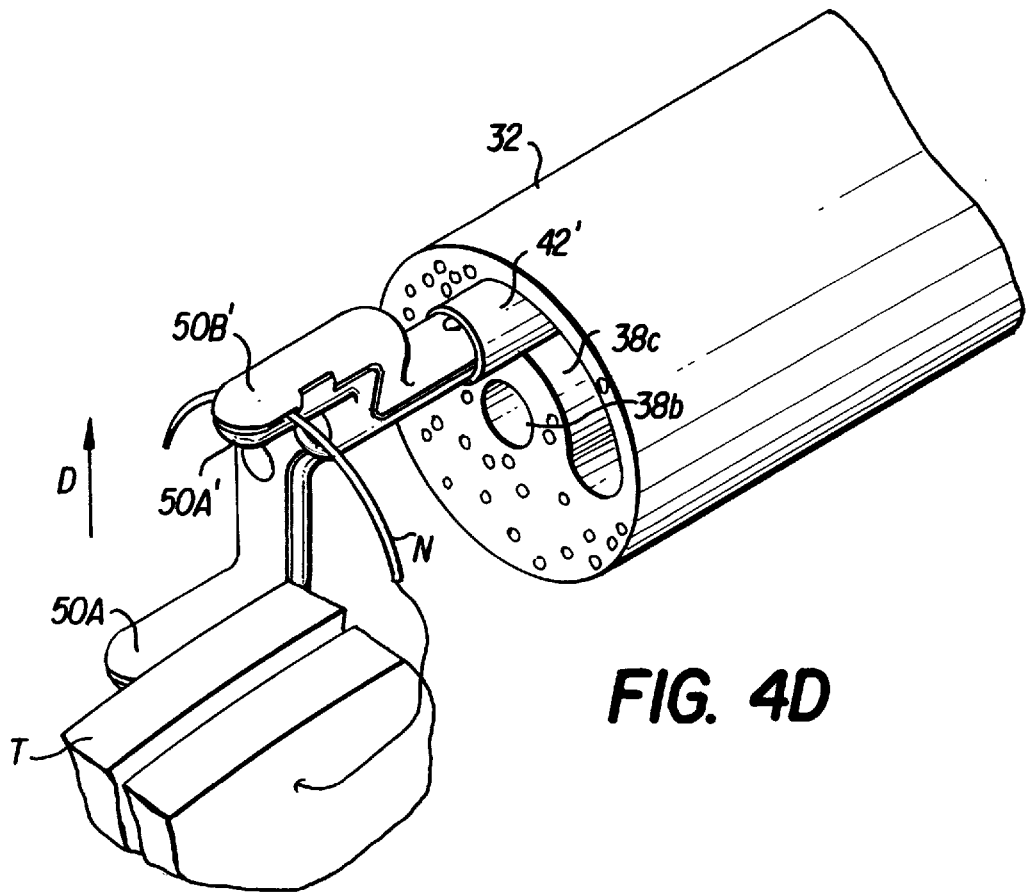
FIG. 4D illustrates a distal end of the first preferred embodiment after having pulled the suture needle through tissue T.
Figure 4E:
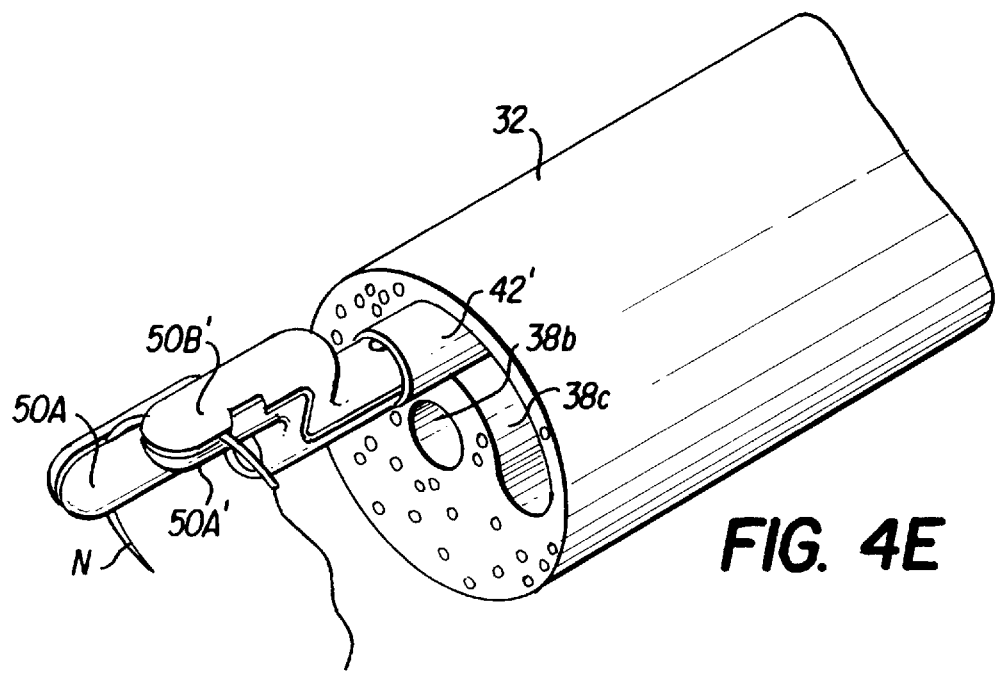
FIG. 4E illustrates a distal end of the first preferred embodiment while transferring the needle for a subsequent stitch.

Arms 51A' and 51B' serve as connecting members between jaw members 50A' and 50B' and inner member 44' and can be made entirely or partly of resilient, flexible or spring materials, or materials having shape memory. Jaw members 50A' and 50B' are biased to be normally disposed to an open position wherein the jaw members have a gap defined therebetween. This permits the shank of a suture needle, or other object, to be received between jaw members 50A' and 50B' and to be grasped thereby. Of course, the inner surfaces of jaw members 50A' and 50B' also can be shaped to correspond to the needle shank, or any other appropriate way, to firmly grasp the needle when the jaw members 50A' and 50B' are in a closed position as shown in FIG. 4D. Cam surfaces 52A' and 52B' are formed on arms 51A' and 51B' respectively to permit closure of jaw members 50A' and 50B' when outer member 42' is advanced distally. Needle catcher 40' also can be designed in various known ways permitting jaw members 50A' and 50B' to be movable between the closed position and the open position.

As illustrated in FIG. 1, proximal controls 60 of the preferred embodiment include two sets of scissor type handle 62 and 64 and 62' and 64' extending out of housing 79 disposed on barrel 32. The handles can be pivoted towards one another to cause movement of the associated pair of jaw members 50A and 50B and jaw members 50A' and 50B' respectively. Button 66 (see FIG. 5) serves to selectively disengage handle 62 and 64 from needle driver 40 and permits handle 62 and 64 to be rotated in concert to a desired orientation, as indicated by arrow C in FIG. 1, without effecting the status of jaws 50A and 50B. This permits the surgeon to orient handles 62 and 64 in a desired manner before or during surgery. Button 66' serves a similar function with respect to handles 62' and 64'.

Figure 5A:
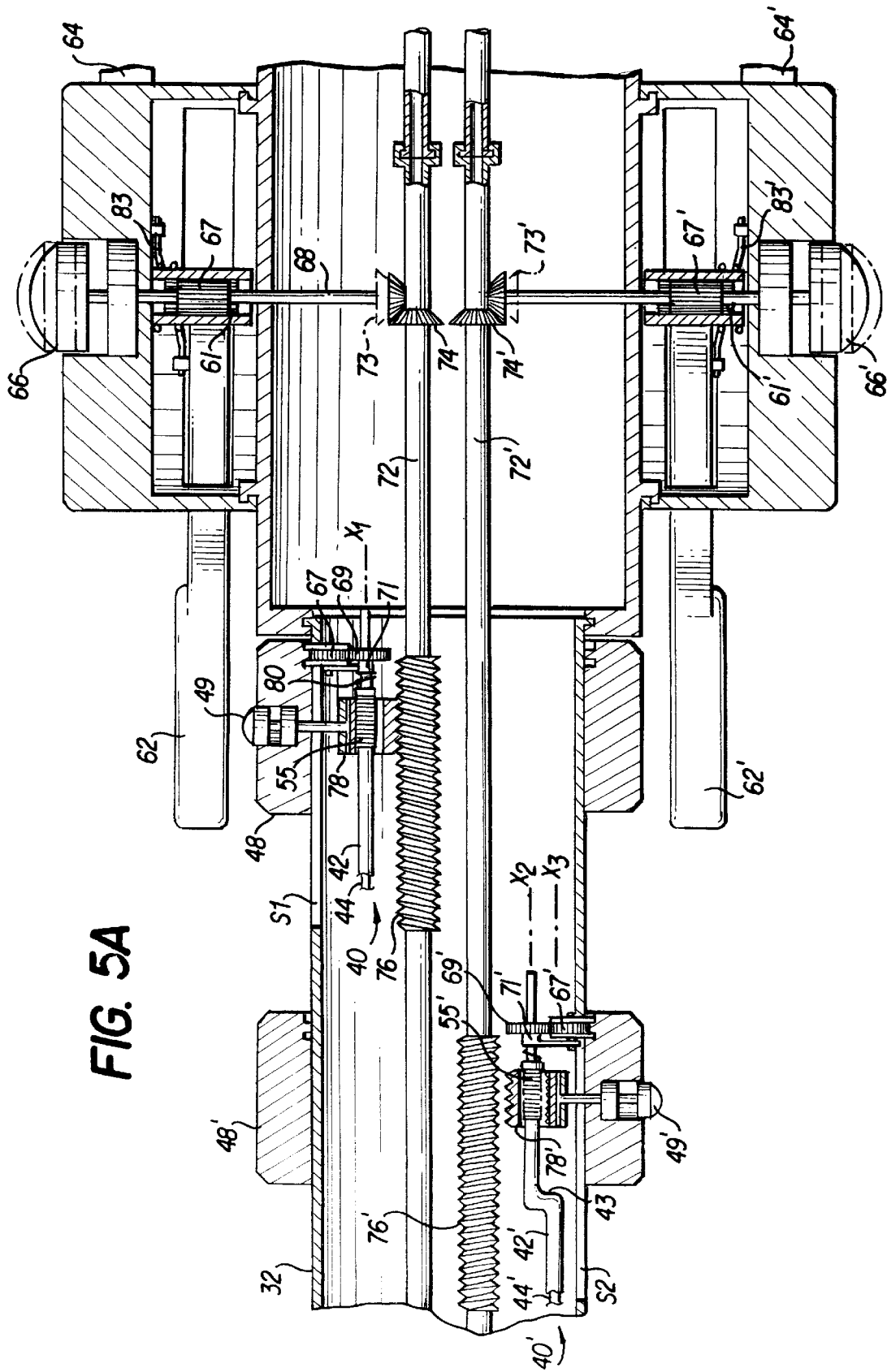
FIG. 5A is a partial sectional view of the first preferred embodiment taken along line 5—5 of FIG. 1 and illustrating the internal mechanism coupling the proximal controls to the drivers.

FIG. 5A illustrates the internal mechanism coupling handle 62 and 64 to needle driver 40. Handles 62 and 64 are biased apart from one another by biasing member 83. A top portion of handle 62 is received in housing 79 and has aperture 61 formed therein. Gear 67 is slidably received in aperture 61 and engages with teeth formed on an inner surface that defines aperture 61. Gear 67 is disposed on shaft 68 which is coupled to button 66. Beveled gear 73 is also disposed on shaft 68. When push button 66 is pressed once, and released, it moves downward in FIG. 5A from the position illustrated by the dotted line to the position illustrated by the solid line. Pressing and releasing button 66 again will return button 66 to the position indicated by the dotted line. Of course, shaft 68, gear 67, and beveled gear 73 move along with button 66.

When button 66 is in the position illustrated by the solid line in FIG. 5, beveled gear 73 is engaged with beveled gear 74 mounted on shaft 72. Therefore, in this position, pressing handle 62 toward handle 64 causes shaft 72 to rotate. When button 66 is in the position illustrated by the dotted line, beveled gear 73 is not engaged with beveled gear 74 to permit handles 62 and 64 to be rotated to a desired orientation without affecting operation of instrument 30.

Button 49 is mounted in knob 48 and operates in a manner similar to button 66. However, operating member 78 is disposed on a stem of button 49. Operating member 78 is essentially cylindrical and has outer gear teeth adapted to be engaged with helical gear 76 disposed on shaft 72 and inner gear teeth adapted to be engaged with teeth of collar 55 disposed on a distal end of needle driver 40. When button 49 is in the position illustrated in FIG. 5, operating member 78 is engaged with helical gear 76 and with collar 55. Accordingly, in this position, rotation of shaft 72 in response to movement of handles 62 and 64 towards one another causes operating member 78 to move proximally along helical gear 76 thus causing outer member 42 to move proximally with respect to inner member 44. Proximal movement of outer member 44, with respect to inner member 42, causes outer member 44 to move off of cam surfaces 52A and 52B to open jaws 50A and 50B. Conversely, releasing handle 62 causes operating member 78, and thus outer member 42 to move distally, due to the force of biasing member 83, thus forcing jaw members 50A and 50B to return to the normally closed position. Therefore, when buttons 66 and 49 are moved inward, as illustrated, compression of handles 62 and 64 causes jaw members 50A and 50B to open. Note that spring 80 biases outer member 42 in the distal direction to normally bias jaws 50A and 50B into the closed position even when needle driver 40 is not engaged with handles 62 and 64.

Proximal controls 60 also include knobs 48 and 48' for causing rotational movement and linear movement of needle driver 40 and needle catcher 40'. Gear 67 extends through slot S1 formed in barrel 32 and is engaged with gear teeth formed on button 48 and gear 69 disposed on inner member 44. When button 49 is pressed and released once to permit operating member 78 to move upward in FIG. 5, operating member 78 is no longer engaged with helical gear 76 or collar 55. In this position, rotation of knob 48 will cause inner member 42 to rotate due to gears 67 and 69. If desired, outer member 42 can be keyed to inner member 44 to rotate along with inner member 44. Accordingly, rotation of knob 48 causes the rotation of the shaft of needle driver 40 about axis $X_1$ and thus causes jaws 50A and 50B, which are offset by arms 51A and 51B, to move through an arcuate path. Also, knob 48 is coupled to inner member 44 and outer member 42 by support assembly 71 which supports gears 67 and 69. Therefore, sliding knob 48 along slot S1 in proximal and distal directions will cause needle driver 40 to also move linearly in proximal and distal directions. Note that when button 49 is pressed and released again to assume the position illustrated in FIG. 5A, operating member 78 is engaged with both helical gear 76 and collar 55 to prevent proximal and distal movement of needle driver 40. Unintentional rotation of needle driver 40 can be prevented by frictional contact or alternatively, a locking pin or the like can be provided to prevent unintentional rotation of knob 48 and needle driver 40.

To rotate needle driver 40, the surgeon presses and releases button 49 so that button 49 is moved upward from the position shown in FIG. 5A. This unlocks knob 48 and permits rotation of knob 48. Then, the surgeon rotates knob 48 to thus rotate gears 67 and 69 and inner member 44. Outer member 42 can be caused to rotate with inner member 44 by frictional contact, splines, or the like, or outer member 42 can remain stationary while inner member 44 rotates.

Proximal controls 60 of the preferred embodiment also include scissor type handles and 62' and 64' extending out of housing 79 which operate in a manner similar to handles 62 and 64. Button 66' serves to selectively disengage handle 62' and 64' from needle catcher 40' and permits handle 62' and 64' to be rotated in concert to a desired orientation without effecting the status of jaws 50A' and 50B'. This permits the surgeon to orient handles 62' and 64' in a desired manner before or during surgery.

As illustrated in FIG. 5A, handles 62' and 64' are biased apart from one another by biasing member 83'. A top portion of handle 62' is received in housing 79 and has aperture 61' formed therein. Gear 67' is slidably received in aperture 61' and engages with teeth formed on an inner surface that defines aperture 61'. Gear 67' is disposed on shaft 68' which is coupled to button 66'. Beveled gear 73' is also disposed on shaft 68'. When push button 66' is pressed once, and released, it moves upward in FIG. 5A from the position illustrated by the dotted line to the position illustrated by the solid line. Pressing and releasing button 66' again will return button 66' to the position indicated by the dotted line. Of course, shaft 68', gear 67', and beveled gear 73' move along with button 66'.

When button 66' is in the position illustrated by the solid line in FIG. 5, beveled gear 73' is engaged with beveled gear 74' mounted on shaft 72'. Therefore, in this position, pressing handle 62' toward handle 64' causes shaft 72' to rotate. When button 66' is in the position illustrated by the dotted line, beveled gear 73' is not engaged with bevel gear 74' to permit handles 62' and 64' to be rotated to a desired orientation without affecting operation of the instrument.

Similar to button 49, member 78' is disposed on a stem of button 49'. Operating member 78' is essentially cylindrical and has outer gear teeth adapted to be engaged with helical gear 76' disposed on shaft 72' and inner gear teeth adapted to be engaged with teeth of collar 55' disposed on a distal end of needle driver 40'. When button 49 is in the position illustrated in FIG. 5A, operating member 78 is not engaged with helical gear 76' and collar 55'. However, when button 49' is pressed and released once, these elements are engaged and, in this position, rotation of shaft 72 in response to movement of handles 62' and 64' towards one another causes operating member 78' to move proximally along helical gear 76' thus causing outer member 42' to move proximally with respect to inner member 44'. Proximal movement of outer member 44', with respect to inner member 42', causes outer member 44' to move off of cam surfaces 52A' and 52B' to open jaws 50A' and 50B'. Conversely, releasing handle 62' causes operating member 78', and thus outer member 42' to move distally, due to the force of biasing member 83', thus permitting jaws 50A' and 50B' to return to the normally closed position. Therefore, when buttons 66' and 49' are moved inward, compression of handles 62' and 64' causes jaw members 50A' and 50B' to open. Note that spring 80' biases outer member 42' in the distal direction to normally bias jaws 50A' and 50B' into the closed position even when needle driver 40' is not engaged with handles 62' and 64'.

As noted above, knob 48' causes rotational movement and linear movement of needle driver 40'. Gear 67' extends through slot S2 formed in barrel 32 and is engaged with gear teeth formed on knob 48' and gear 69' disposed on inner member 44'. When knob 49' is pressed and released to place operating member 78' in the position illustrated in FIG. 5, operating member 78' is not engaged with helical gear 76' or collar 55'. In this position, rotation of knob 48' will cause inner member 42' to rotate due to gears 67' and 69'. If desired, outer member 42' can be keyed to inner member 44' to rotate along with inner member 44'. Accordingly, rotation of knob 48' causes the rotation of proximal portions of the shaft of needle catcher 40' about axis $X_2$ and thus causes distal portions of the shaft, which are offset by bent portion 43, to move through groove 38c in an arcuate path. Also, knob 48' is coupled to inner member 44' and outer member 42' by support assembly 71' which supports gears 67' and 69'. Therefore, sliding knob 48' along slot S2 in proximal and distal directions will cause needle catcher 40' to also move linearly in proximal and distal directions. Note that when button 49' is pressed and released again, operating member 78' is engaged with both helical gear 76' and collar 55' to prevent proximal and distal movement of needle driver 40'. Unintentional rotation of needle catcher 40' can be prevented by frictional contact or alternatively, a locking pin or the like can be provided to prevent unintentional rotation of knob 48' and needle catcher 40'.

To rotate needle catcher 40' about axis $X_2$, the surgeon presses and releases button 49' so that button 49' is moved to the position shown in FIG. 5. This unlocks knob 48' and permits rotation of knob 48'. Then, the surgeon rotates knob 48' to thus rotate gears 67' and 69' and inner member 44'. Outer member 42' can be caused to rotate with inner member 44' by frictional contact, splines, or the like, or outer member 42' can remain stationary while inner member 44' rotates.

As noted above, angled cam surfaces 52A' and 52B' are formed on outer surfaces of arms 51A and 51B respectively (see FIG. 3A), at positions near the distal end of outer member 42. When outer member 42 is biased distally over cam surfaces 52A and 52B jaw members 50A and 50B are pressed toward one another to the closed position. Therefore, compression of handles 62 and 64 opens jaw members 50A and 50B. Cam surfaces 52A and 52B can be formed by bent portions defined on legs 51A and 52B or by separate elements that are attached to, or formed on, legs 51A and 51B. Release of handles 62 and 64 causes jaw members 50A and 50B to return to the closed position due to the biasing force of biasing member 83 and spring 80. Lock protrusions 63 and 65 are disposed on handles 62 and 64 respectively. Lock protrusions 63 and 65 are serrated to interlock and allow the position of handles 62 and 64 to be maintained in a state corresponding to a desired position of jaw members 50A and 50B. Lock protrusions 63 and 65 can be pivoted to a position at which they will not interlock if desired. Note that handles 62 and 64 are configured to be grasped while the surgeon's fingers pass through openings in the handles or while the surgeon's fingers are wrapped around outer portions of the handles to increase comfort and adaptability. Further, spring 80 biases outer member 42 distally to maintain jaw members 50A and 50B in a closed state when handles 62 and 64 are not coupled to outer member 42 because of disengagement between bevel gears 70 and 74 or between operating member 78 and helical gear 76.

Also, angled cam surfaces 52A' and 52B' are formed on outer surfaces of arms 51A' and 51B' respectively (see FIG. 3B), at positions near the distal end of outer member 42'. When outer member 42' is biased distally over cam surfaces 52A' and 52B' jaw members 50A' and 50B' are pressed toward one another to the closed position. Therefore, compression of handles 62' and 64' opens jaw members 50A' and 50B'. Cam surface 52A' and 52B' can be formed by bent portions defined on legs 51A' and 52B' or by separate elements that are attached to, or formed on, legs 51A' and 51B'. Release of handles 62' and 64' causes jaw members 50A' and 50B' to return to the closed position due to the biasing force of biasing member 83' and spring 80'. Lock protrusions 63' and 65' are disposed on handles 62' and 64' respectively. Lock protrusions 63' and 65' are serrated to interlock and allow the position of handles 62' and 64' to be maintained in a state corresponding to a desired position of jaw members 50A' and 50B'. Lock protrusions 63' and 65' can be pivoted to a position at which they will not interlock if desired. Note that handles 62' and 64' are configured to be grasped while the surgeon's fingers pass through openings in the handles or while the surgeon's fingers are wrapped around outer portions of the handles to increase comfort and adaptability. Further, spring 80' biases outer member 42' distally to maintain jaw members 50A' and 50B' in a closed state when handles 62' and 64' are not coupled to outer member 42' because of disengagement between bevel gears 70' and 74' or between operating member 78' and helical gear 76'.

Figure 5B:
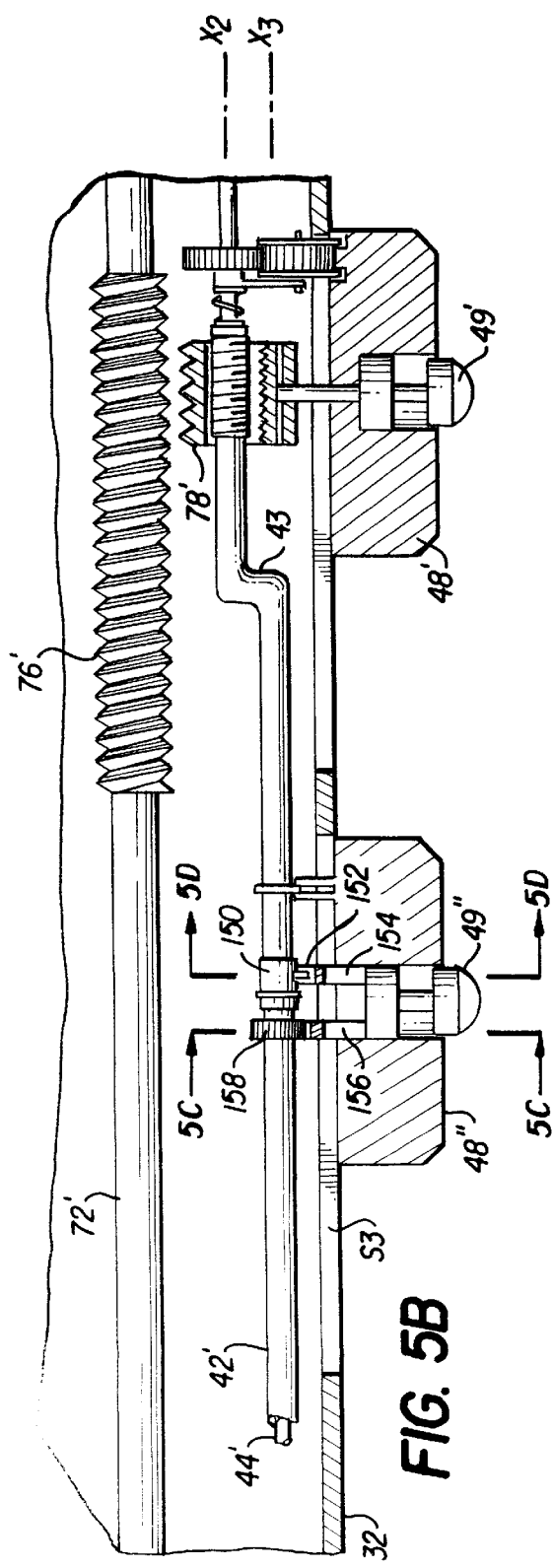
FIG. 5B illustrates the internal mechanism for rotating the needle catcher about axis $X_3$, in partial section.

Needle catcher 40' can also be rotated about axis $X_3$ indicated in FIGS. 3B and 5A. Knob 48" is also disposed on barrel 32 and button 49" extends through knob 48", as illustrated in FIG. 5B. Rotational coupling 150 is disposed between distal and proximal portions of inner member 44' and outer member 42' to permit the distal and proximal portions to rotate with respect to one another when button 152 of rotational coupling 150 is depressed. When button 152, which is biased outwardly, is not depressed, distal and proximal portions of the shaft are rigidly coupled to one another. Arcuate rack 156 (see FIG. 5C) and arcuate operating member 154 (see FIG. 5D) are disposed on an inner portion of button 49". When button 49" is moved outward, i.e. downward in FIG. 5B, rack 156 and operating member 154 do not engage with the shaft of needle catcher 40' to allow the normal operation described above. When button 49" is depressed, i.e. moved upward in FIG. 5B, rack 156 is engaged with gear 158 disposed on outer member 42' and operating member 154 depresses button 152 to unlock rotational coupling 150. In this state, rotation of knob 48 will cause outer member 42 and inner member 44 to rotate about axis $X_3$.

It will be appreciated that the jaw members of needle driver 40 and needle catcher 40' can be of different configurations, such as those described below, dependent upon procedural use and other considerations. Also, cutting elements 53 can be provided on the jaw members as needed to cut suture material or tissue. Further, as noted above, any appropriate end effector can be used in place of, or in combination with jaws on one or both of the drivers.

Channel 38b can be used as operating channels for suction devices, irrigation devices, or any other appropriate instrument such as a cautery device or the like. Also, aperture 70 is formed in a position of arm 51B that is proximal a distal end of inner member 44 to define an operating channel through needle driver 40 and aperture 70' is formed in arm 51B' to define an operating channel through needle catcher 40' (see FIG. 4B, for example).

In use, a distal end of suturing instrument 30 is inserted into a body cavity using known techniques, while needle driver 40 and needle catcher 40' are in the insertion position, or parked position, illustrated in FIG. 4A. Note that the entire device can be inserted through a single puncture site. Also, in this position, jaw members 50A and 50B and 50A' and 50B' as well as needle N are disposed within the diametrical dimension of barrel 32 because the respective arms are crossed over one another.

Figure 13A:
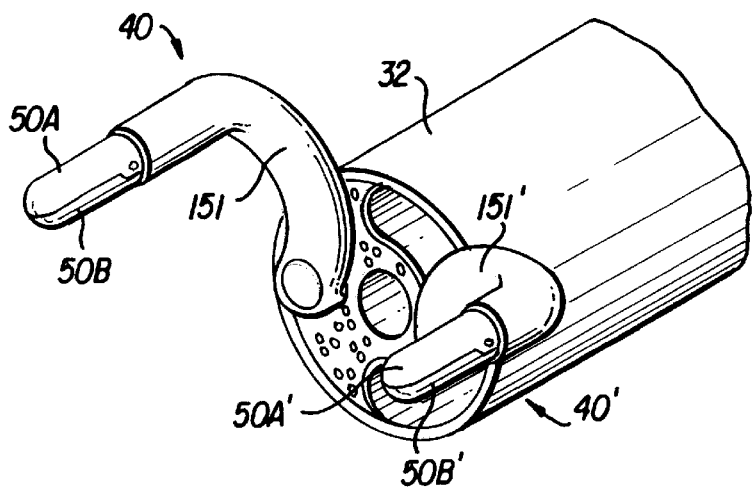
FIG. 13A illustrates a distal end of a ninth preferred embodiment of the invention in an operating position.
Figure 13B:
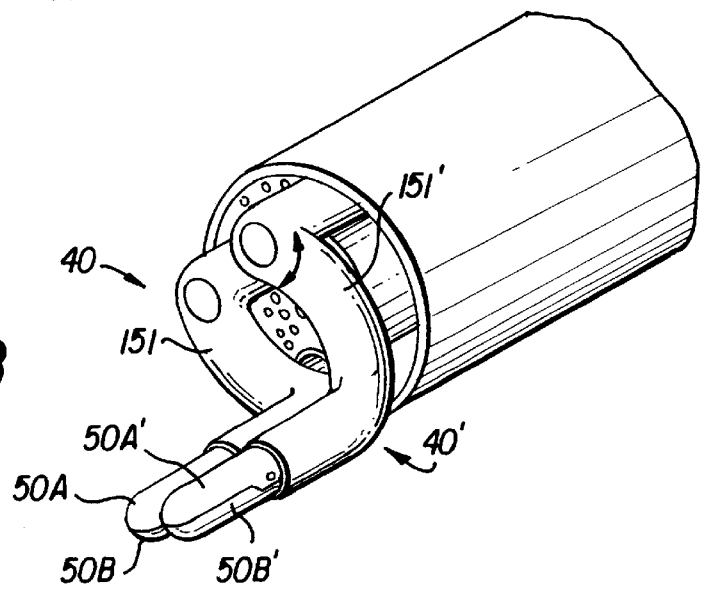
FIG. 13B illustrates a distal end of a ninth preferred embodiment of the invention in an insertion or parked position.

Of course, the arms can be in any position of which the end effectors are contained within the dimensions of the barrel, such as the position illustrated in FIG. 13B with respect to another embodiment. Further, in open surgery, the arms can be in any position during insertion. By grasping proximal controls 60, the distal end of suturing instrument 30 is guided to the operative site through a portal sleeve positioned in the wall of an anatomical cavity (in the case of minimally invasive surgery). The portal sleeve can be positioned in the anatomical cavity wall using any suitable penetrating technique, including those creating puncture sites by means of removable obturator, such as trocars, and can include a valve housing, if desired, to prevent loss of pneumoperitoneum during insertion and withdrawal of the instrument. Further, retractable sheath 54, which is illustrated in phantom in FIG. 4A, (or any appropriate structure) can be provided to facilitate insertion through a portal sleeve valve by covering needle driver 40 and needle catcher 40'. Visualization of the procedure can be accomplished using a conventional endoscope incorporated into channel 38b, for example (known as a single puncture procedure) or separately positioned within the anatomical cavity through a second portal sleeve located at another puncture site (known as a double puncture procedure).

Prior to insertion through a portal sleeve or the like, with button 66 in the position illustrated by the solid line in FIG. 5, button 66 is pressed and released and handles 62 and 64 are oriented at the desired angle. Then button 66 is pressed and released again and handles 62 and 64 are pressed together by the surgeon so that jaw members 50A and 50B are opened to receive needle N. Then, handles 62 and 64 are released so that needle N is held tightly between jaw members 50A and 50B of needle driver 40. Handles 62' and 64' are oriented similarly. Alternatively, needle N can be introduced into the body cavity by a separate instrument through a separate puncture sight or through channel 38b. In this embodiment, needle N is of a semi-circular configuration. However, needle N can be straight or of any other appropriate shape. Prior to suturing, needle catcher 40' is set to receive the tip of needle N by compressing handle 62' and 64' and thus moving jaw members 50A' and 50B' to the open position. Lock protrusions 63' and 65' can be engaged to maintain jaws 50A' and 50B' in the open position. This is accomplished by squeezing handles 62' and 64' together. Referring to FIGS. 4A–4E, which illustrate a suturing process after insertion of the distal end, the shaft of needle holder 40 is rotated in a counter-clockwise direction, by rotating knob 48, as viewed in FIG. 4A to the position indicated in FIG. 4B and the shaft of needle catcher 40' is rotated about axis $X_3$ in a clockwise direction, by rotating knob 48", to the position illustrated in FIG. 4B to permit anatomical tissue T, which is to be sutured, to be positioned between the tip of needle N and jaw members 50A' and 50B' of needle catcher 40'. Also note that one or both of needle driver 40 and needle catcher 40' can also be advanced distally, by pressing button 49 and 49' and sliding knobs 48 and 48', to avoid interference with one another and to facilitate the procedure, as illustrated in FIG. 4B. Subsequently, the shaft of needle driver 40 is rotated further in a counter-clockwise direction, by rotating knob 48, to drive needle N through a portion of the tissue while jaw members 50A' and 50B' of needle catcher 40' support the tissue from an opposite side as illustrated in FIG. 4C. A tip of needle N is thus caused to pass between jaw members 50A' and 50B' of the needle catcher 40' as shown in FIG. 4C.

With needle N positioned in needle catcher 40', handles 62' and 64' are released by the surgeon to grasp needle N between jaw members 50A' and 50B'. Handles 62 and 64 are then moved toward one another, to place jaw members 50A and 50B in the open position and thus release needle N from needle driver 40. Subsequently, the shaft of needle catcher 40' can be moved arcuately, i.e. rotated about axis $X_2$, in a clockwise direction, by rotating knob 48', to the position shown in FIG. 4D and the shaft of needle driver 40 can be rotated in a clockwise direction to receive the needle again at the position shown in FIG. 4E. At any time the position of needle catcher 50 can be adjusted with knob 48", i.e. rotated about axis $X_2$, to facilitate the procedure. Alternatively, the shaft of needle catcher 40' can be moved arcuately through groove 38c and the shaft of needle driver 40 can be rotated to pass the needle back to needle driver 40 at another location. Jaw members 50A' and 50B' can be opened, by compressing handles 62' and 64', and jaw members 50A and 50B can be closed and the shaft of needle driver 40 can be rotated back in the counter-clockwise direction to pull needle N out of needle catcher 40'. A second stitch can be made in a manner similar to the first stitch.

It is clear from the drawings that the movement of the needle is through an arcuate path that extends beyond the diameter of barrel 32 and corresponds to the natural path of the needle through tissue. This provides a large working span and does not damage tissue. Also, this movement is accomplished merely by rotating knobs 48 and 48' (and 48" if desired). Note that needle N can be straight or curved. Also, suture S can be connected to any portion of needle N and can be stored in operating channel 38b with or without needle N. Further, suturing and manipulation can be accomplished by rotating barrel 32 in its entirety with the needle holders locked in position relative to barrel 32. For example, outer member 42 can be locked relative to barrel 32 by engagement with operating member 78 or by a locking pin or the like and barrel 32 can be rotated to drive needle N through tissue. Alternatively, needle driver 40 can be fixed rotationally relative to barrel 32 in a permanent manner.

At any point during the procedure, channel 38b can be used for irrigation or aspiration, can serve as a space for holding suture material S and/or needle N or as a portal for the introduction of other medical instruments such as, forceps, cutting members, ligators, or cautery devices. Also, channel 38a and slot 38c can be used for irrigation, aspiration, insertion of an instrument or the like by utilizing the passage through inner member 44 of needle driver 40 and/or through inner member 44' of needle catcher 40'. Proximal apertures 90–92 are provided for access to operating channels 38a and 38b and groove 38c respectively. Further, any of these channels can be used for insertion of an endoscope or other viewing instrument.

In the suturing method described above, needle N is grasped further along the shank thereof in each stitch. Therefore, the number of consecutive stitches that can be made is limited by the length of needle N. A retractable plate can be provided, through one of the operating channels for example, to push the needle further into the jaws.

Alternatively, to replace needle N in needle driver 40, the distal end of instrument 30 can be raised from the position illustrated in FIG. 4D, as indicated by arrow D. Subsequently, needle catcher 40' can be moved in the clockwise direction through slot 38c, to place needle N between jaws 50A and 50B of needle driver 40. Instrument 30 is then ready for a subsequent stitch or other procedure. In addition, if both axial ends of needle N are provided with sharp, tissue penetrating tips, it is possible to penetrate the anatomical tissue at multiple locations in order to form a continuous run of stitches merely by manipulating needle catcher 40' and needle driver 40 in a "shuttle" manner, i.e. passing the needle back and forth through the tissue in alternating directions.

Needle driver 40 and needle catcher 40' can be modified to suture anatomical tissue with straight or slightly curved suture needles by shaping the jaw members appropriately to receive and hold the needle. Also, the jaw members can be rotatable on the arms to accept needle N more smoothly. Further, known knotting elements, such as knotting element 96 shown in FIG. 7D can be used in lieu of traditional knotting techniques during the suturing procedure. Some examples of suitable knotting elements for this purpose are described in pending applications Ser. Nos. 08/366,285, filed Dec. 29, 1994; 08/377,723, filed Jan. 25, 1995; 08/401, 002, filed Mar. 9, 1995; and 08/585,875, filed Jan. 16, 1996 the disclosures of which are incorporated herein by reference. Further, needle N can be held between jaws 50A and 50B while extending along the lengthwise direction of instrument 30 during insertion. In this case needle N can be seated in grooves formed along grasping surfaces of jaw members 50A and 50B or jaw members 50A' and 50B'.

From the above, it will be appreciated that the instrument according to the present invention permits suturing of anatomical tissue or other procedures without the need of having to use multiple needle holding instruments inserted through multiple puncture sites. Needle driver 40 and needle catcher 40' each are movable and operable to grasp and release a suture needle N so that the suture needle N can be driven through anatomical tissue positioned between needle driver 40 and needle catcher 40', and can be moved to pull the suture material through the anatomical tissue with a large working span. Either one or both of needle driver 40 and needle catcher 40' can be movable through an arcuate slot.

Figure 6A:
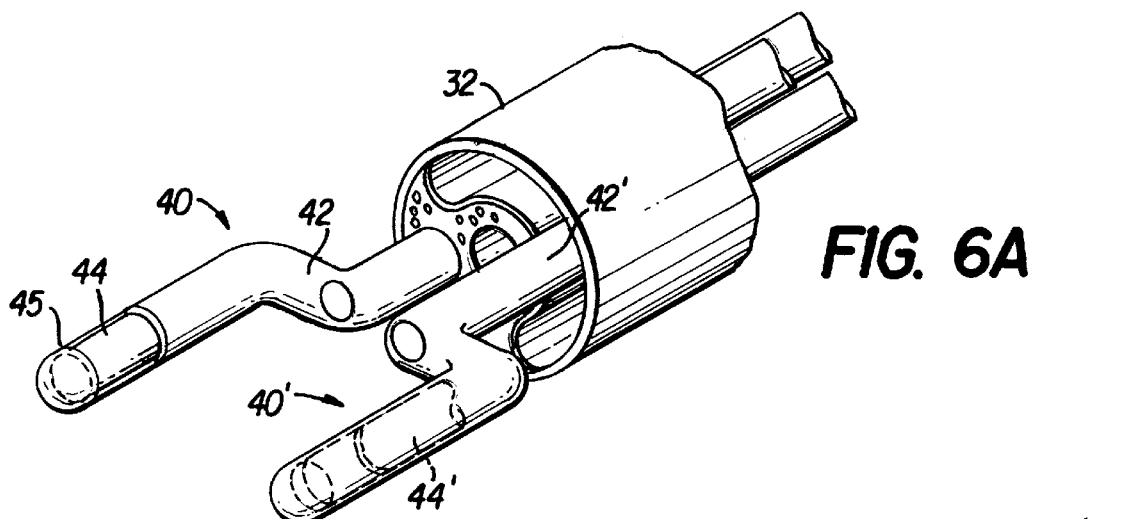
FIG. 6A illustrates a distal end of a second preferred embodiment of the invention with needle holders in the closed position.
Figure 6B:
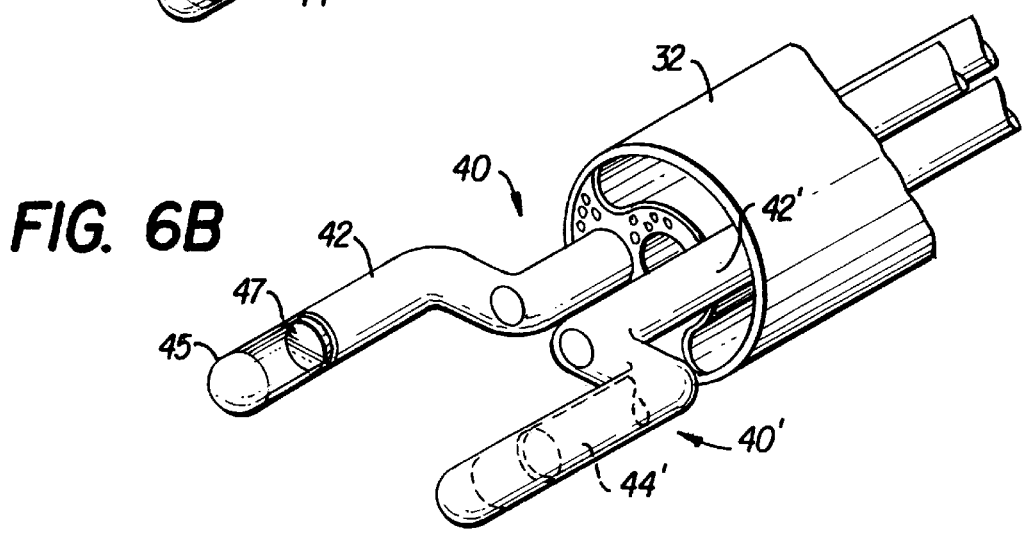
FIG. 6B illustrates a distal end of the second preferred embodiment of the invention with the needle holders in an open position.

FIG. 6A and 6B illustrate a second embodiment having needle driver 40 in which inner member 44 is resiliently flexible and outer member 42 has notch 45 formed therein. Movement of inner member 44 in the distal direction serves to grasp a needle or other object placed in notch 45 in the closed position illustrated in FIG. 6A. FIG. 6B illustrates the open position of which inner member 44 is retracted proximally. Inner member 44 has abutment surface 47 on a distal end thereof. Abutment surface 47 can have grooves or any other pattern formed therein to grasp needle N with a desired orientation. Also, the angle of abutment surface 47 can be varied to grasp needle N in a desired manner. Inner member 44 can be rotatable with respect to outer member 42 to position a needle or other object.

Similarly, needle catcher 40' has flexible inner member 44' and outer member 42' having notch 45. Other aspects and the operation of this embodiment are similar to the first embodiment. For example, the mechanisms for rotating the drivers and moving the inner and outer members relative to one another can be similar to the mechanisms discussed above.

Figure 7:
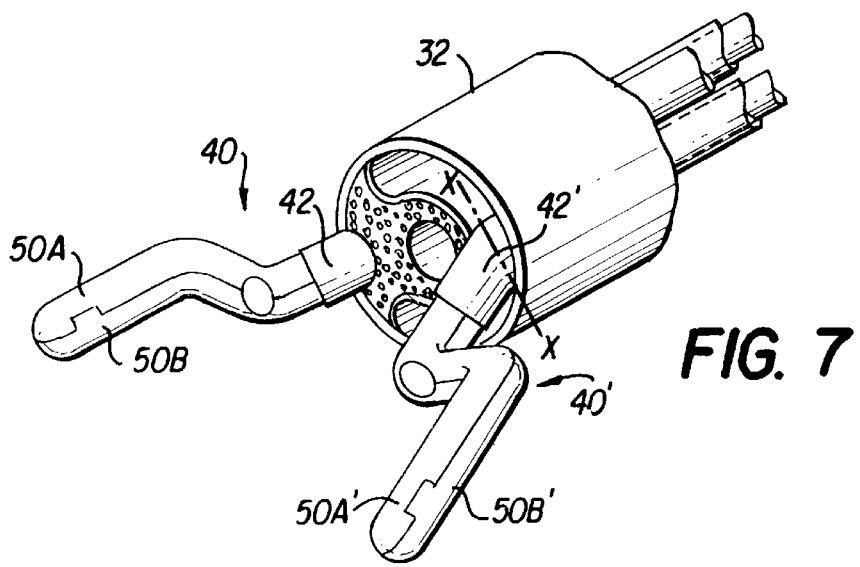
FIG. 7 illustrates a distal end of a third preferred embodiment of the invention.

FIG. 7 illustrates a third embodiment in which needle catcher 40' is resiliently flexible, is normally bent outward at line x-x, and can be drawn proximally into barrel 32 to be straightened out. In a free state, needle catcher 40' of FIG. 7 is angled as shown. Of course this configuration can be applied to a needle driver also. Suturing can be accomplished in the manner described above. Additionally, the needle can be passed through tissue by causing needle catcher 40' to bend back and forth by drawing the shaft into and extending the shaft out of barrel 32.

FIGS. 8A and 8B illustrate a distal end of a fourth embodiment having needle holders that include hooked member 41 and 41' and sliding keeper 43 and 43' that can be moved distally and proximally with respect to hook member 41 and 41'. A needle or other object can be grasped when keeper 43 is advanced distally from the open position illustrated in FIG. 8A to the closed position illustrated in FIG. 8B. Note that a cutting blade can be defined on a portion of a distal end of keeper 43 and 43' and notch 47 and 47' can be defined in hook member 41 and 41'. Suture material, or any other material, can be cut by being placed in notch 47 and 47' and subsequently advancing keeper 43 and 43' distally.

A fifth embodiment illustrated in FIGS. 9A and 9B has pivoting jaw members. Instrument 30 includes needle driver 40 and needle catcher 40'. Needle driver 40 includes outer member 42, inner member 44 disposed in outer member 42, and jaw members 50A and 50B coupled to a distal end of inner member 44. Outer member 42 has a bent perpendicular segment disposed perpendicularly or angularly to a main body of outer member 42 and an offset distal segment extending from the angled segment and disposed parallel to the main body of the outer member 42. Both the bent segment and the distal segment extend out of a distal end of barrel 32. A channel extends entirely through outer member 42 including the bent segment and the distal segment.

Inner member 44 includes a main body disposed in the main body of outer member 42, a bent perpendicular segment disposed in the bent segment of outer member 42 and a Y-shaped segment 145 disposed in the distal segment of outer member 42. A passage extends entirely through the main body of inner member 44 in axial or longitudinal alignment with aperture 70 formed in the angled segment of the outer member 42 such that ligator 80, or another instrument, can pass therethrough. The bent segments of inner member 44 and outer member 42 define an arm or connecting member between the shaft and offset jaws.

Y-shaped segment 145 has outwardly extending portions 147 that are pivotally connected to legs 149A and 149B extending from jaw members 50A and 50B, respectively. Legs 149A and 149B are angled inwardly from their respective jaw members to overlap one another in cross-wise fashion. Proximal ends of legs 149A and 149B are pivotally connected to extending portions 147, respectively, at pivots. These pivots also permit extending portions 147 to slide axially along legs 149A and 149B. Legs 149A and 149B are pivotally connected to one another, where they cross, by a pivot. This pivot is fixedly secured to outer member 42. Inner member 44 is slidably disposed in outer member 42 to permit longitudinal movement relative thereto.

There is adequate clearance between the bent segment of inner member 44 and the bent segment of outer member 42 to permit inner member 44 to be moved proximally and distally, relative to outer member 42. When inner member 44 is moved in the proximal direction, jaw members 50A and 50B are placed in the closed position by the pivoting motion of legs 149A and 149B, as illustrated in FIG. 9A. On the other hand, when inner member 44 is moved in the distal direction, jaw members 50A and 50B are placed in the open position by the pivoting motion of legs 149A and 149B, as illustrated in FIG. 9B. Of course, relative movement of inner member 44 can be accomplished by proximal end controls in the manner disclosed above, or in any other appropriate manner. A slot can be formed in a distal end of outer member 42 to permit ends of legs 149A and 149B to extend out of outer member 42, in a radial direction thereof, when jaw members 50A and 50B are in the open position, if necessary. This permits a greater stroke of jaw members 50A and 50B. The jaws of needle catcher 40' can operate in a similar manner and like parts of needle catcher 40' are labeled with like reference numerals with the added suffix "'".

Figure 10A:
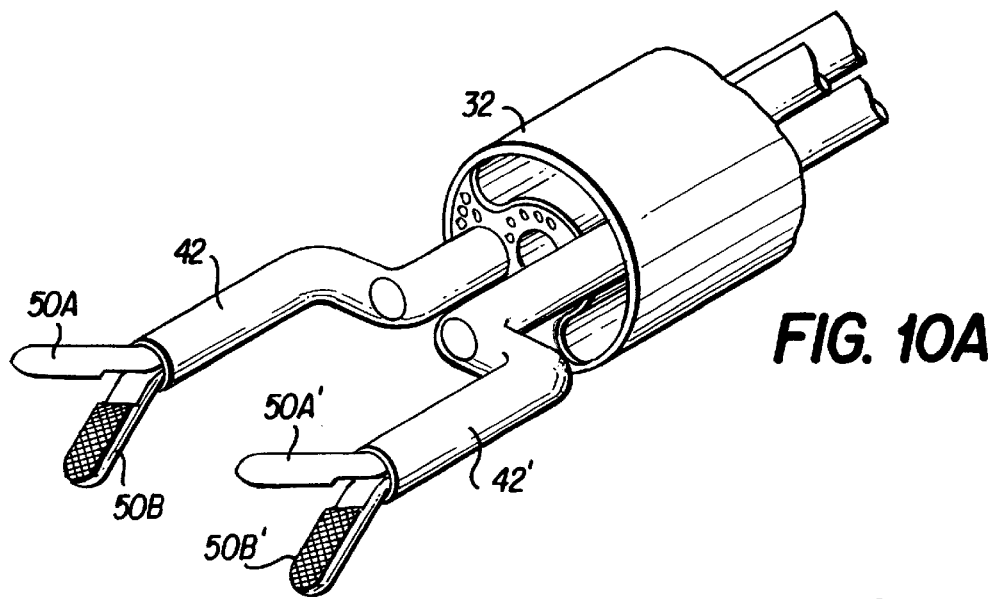
FIG. 10A illustrates a distal end of a sixth preferred embodiment of the invention with jaws in the open position.
Figure 10B:
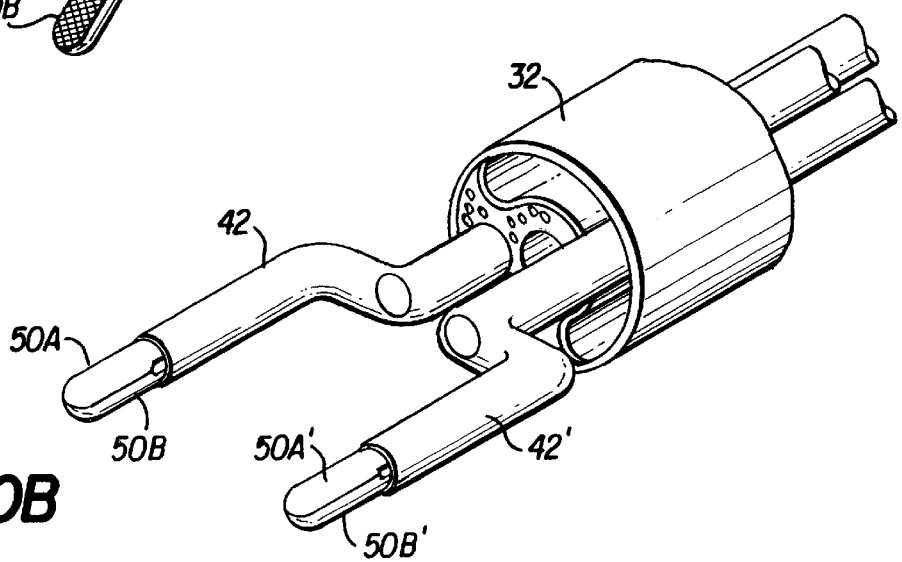
FIG. 10B illustrates a distal end of the sixth preferred embodiment of the invention with jaws in the closed position.

FIGS. 10A and 10B illustrate the distal end of a sixth embodiment having drivers 40 and 40' with forceps jaw members 50A and 50B and 50A' and 50B' respectively. Inner member 44 of this alternative arrangement is similar to inner member 44 of the first embodiment illustrated in FIG. 1. However, outer member 42 of this arrangement extends around arms 51A and 51B to jaws 50A and 50B. Similarly, outer member 42' extends to jaw members 50A' and 50B'. There is adequate clearance between outer member 42 and inner member 44 to permit outer member 42 to move proximally and distally with respect to inner member 44 to open and close jaws 50A and 50B. The same holds true for outer member 42' and inner member 44'. Alternatively, inner members 44 and 44' can be made at least partly of a flexible resilient or shape memory material to permit movement distally and proximally with respect to outer member 42 and 42' respectively. Other aspects of this arrangement are similar to the device illustrated in FIG. 1. The arms are illustrated as lying in the same plane. However, similar to the device described above, drivers 40 and 40' are movable distally and axially and thus the arms can be placed in different planes to permit the arms to be crossed as noted above. Also note that jaw members 50A and 50B and 50A' and 50B' are oriented to facilitate manipulation of tissue, as opposed to suturing. Of course, the jaw members can be replaced by any desired end effector or can be oriented for suturing or other procedures.

Figure 11A:
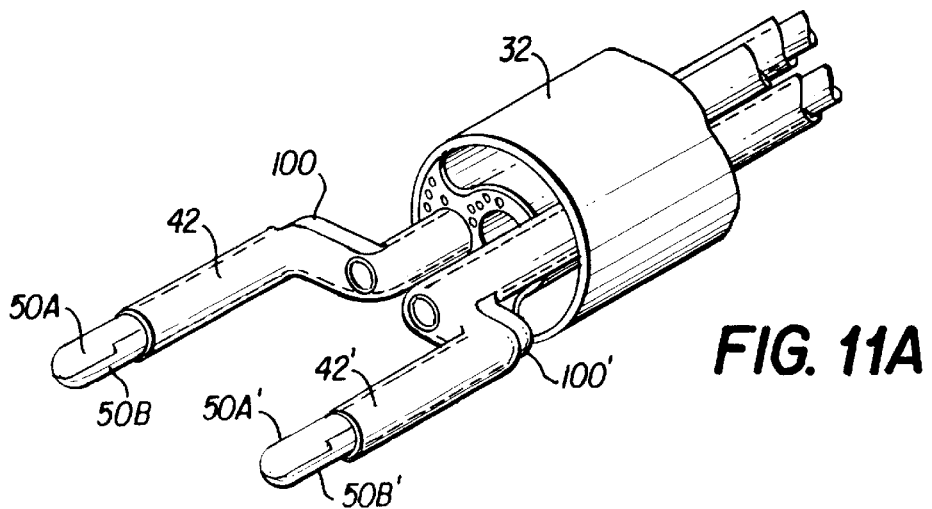
FIG. 11A illustrates a distal end of a seventh preferred embodiment, in partial section, with jaws in a closed position.
Figure 11B:
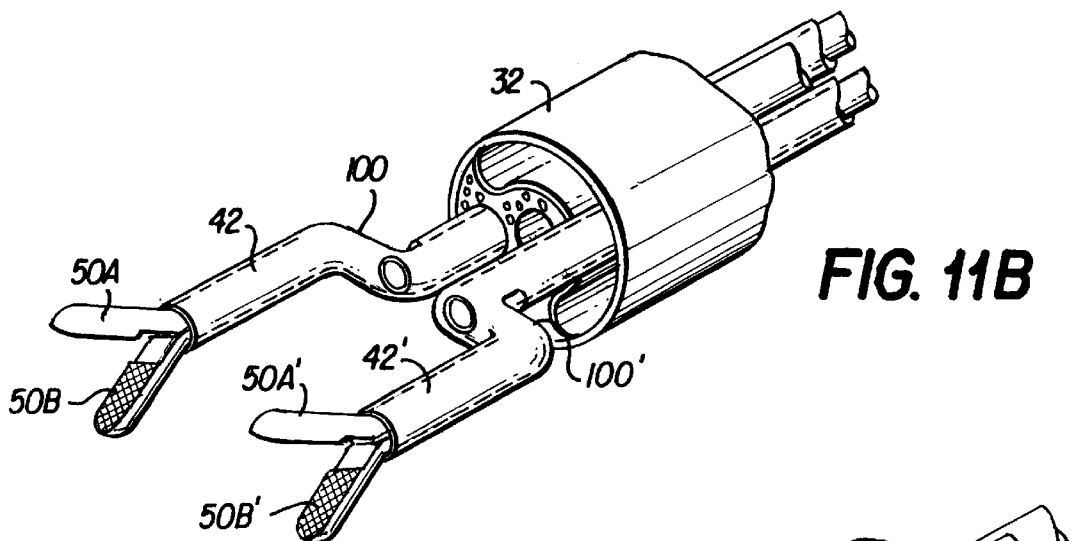
FIG. 11B illustrates a distal end of the seventh preferred embodiment, in partial section, with jaws in the opened position.

FIGS. 11A and 11B illustrate a seventh embodiment that is similar to that of FIGS. 10A and 10B except for slots 100 and 100' which are formed in proximal portions of the arms. When inner members 44 and 44' are moved proximally with respect to outer members 42 and 42' to place the jaw members in a closed position, inner members 44 and 44' can protrude respectively out of slots 100 and 100' defined in outer members 42 and 42' (see FIG. 11A). This arrangement permits a longer stroke of relative movement between the inner members and the outer members without the need to reduce the size of the inner member unnecessarily. FIG. 11B illustrates the open position of the jaw members.

Figure 12A:
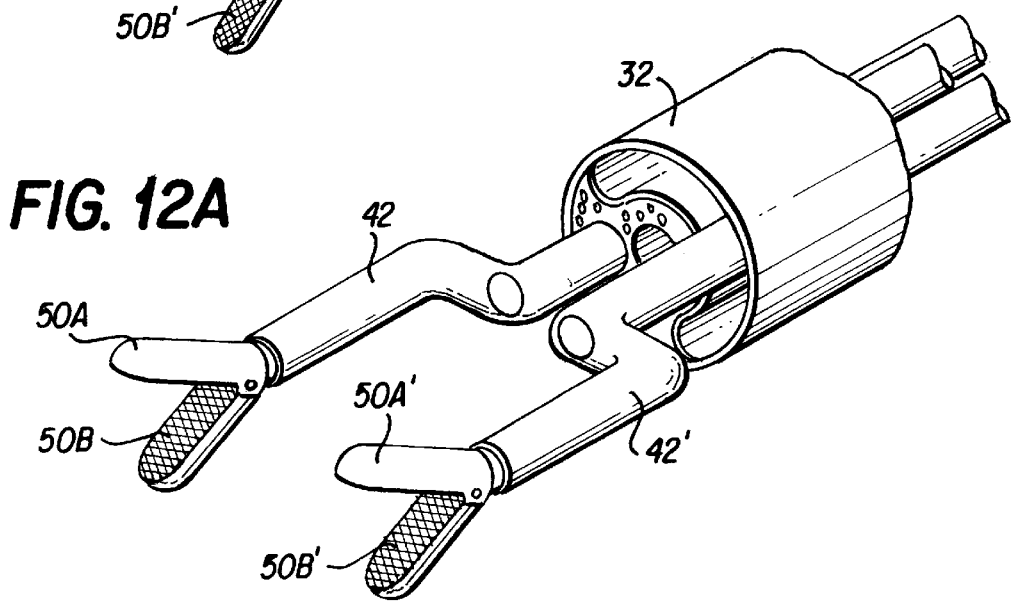
FIG. 12A illustrates a distal end of an eighth preferred embodiment of the invention with jaws in the opened position.
Figure 12B:
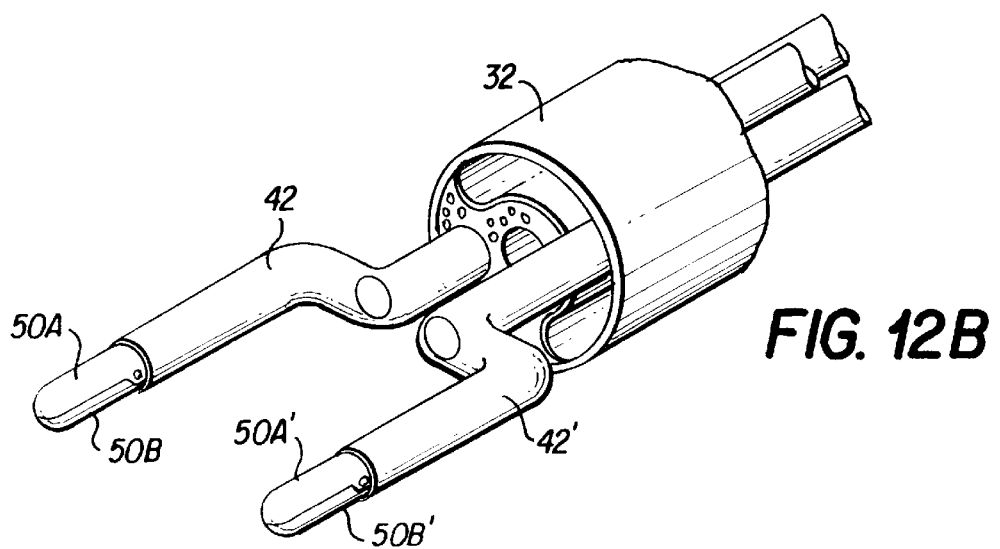
FIG. 12B illustrates a distal end of the eighth preferred embodiment with jaws in the closed position.

FIGS. 12A and 12B illustrate an eighth embodiment in which pivoting jaws are disposed on a distal end of inner member 44. Movement of outer member 42 distally with respect to inner member 44 pushes jaws 50A and 50B to the closed position illustrated in FIG. 12B. Of course, driver 40' operates in a similar manner. Other aspects of this alternative arrangement are similar to the embodiment illustrated in FIGS. 10A and 10B.

Figure 13C:
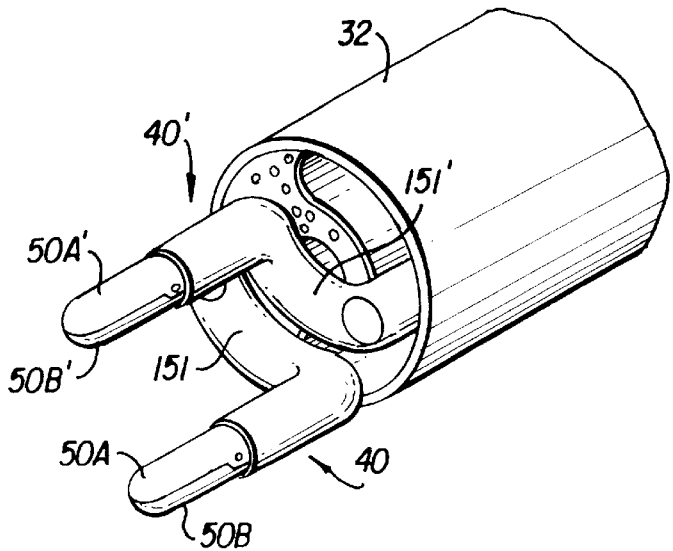
FIG. 13C illustrates a distal end of the ninth preferred embodiment of the invention in an alternative insertion or parked position.

A suturing instrument according to a ninth embodiment is illustrated in FIGS. 13A, 13B, and 13C. This embodiment includes needle driver 40 and needle catcher 40' and is similar to the embodiment of FIGS. 12A and 12B, with pivoting jaws, except for the configuration of arms 151 and 151'. Specifically, arms 151 and 151' are curved to correspond substantially with the curvature of the circumferential outer surface of barrel 32. Jaw members 50A and 50B are moveably mounted on a distal end of inner members respectively to open and close in a manner similar to the embodiment of FIGS. 12A and 12B disclosed above. Once again, like parts of needle catcher are distinguished by the suffix "'". FIG. 13A shows an operating position and FIGS. 13B and 13C show insertion positions in which the jaws are contained within the diametrical dimensions of barrel 32.

This embodiment can be used to suture tissue in a manner similar to the first embodiment. However, the insertion position of this embodiment, in which the arms and jaw members are contained within the diametrical dimension of barrel 32 (see FIGS. 13B and 13C) does not require that the arms cross one another. Therefore, the arms need not be disposed in different planes, but can be movable in the distal and proximal directions if desired. In operation, a needle may be grasped by the jaw members and passed through tissue in a manner similar to the embodiments discussed above. Also, the jaw members and shafts of this embodiment can be manipulated in the same way as the other embodiments discussed above.

Figure 14A:
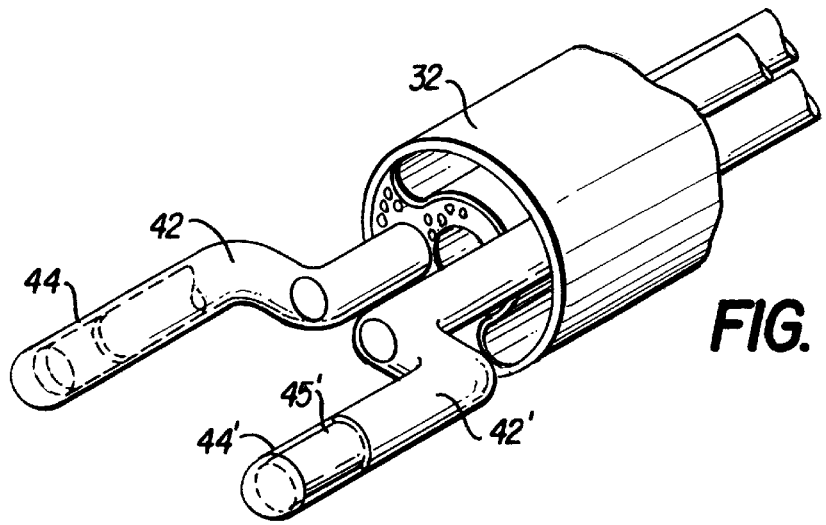
FIG. 14A illustrates a distal end of a tenth preferred embodiment of the invention with needle holders in the closed position.
Figure 14B:
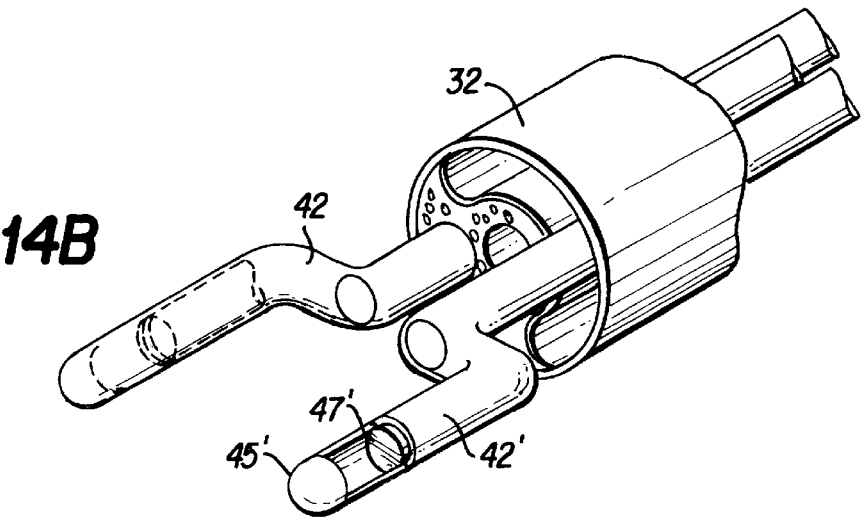
FIG. 14B illustrates a distal end of a tenth preferred embodiment of the invention with needle holders in an open position.

FIGS. 14A and 14B illustrate a tenth embodiment that is similar to the embodiment illustrated in FIGS. 6A and 6B. However, in this embodiment, slots 45 and 45' face outward when needle driver 40 and needle catcher 40' are in the illustrated position. Of course, the orientation and size of slots 45 and 45' can be varied based upon practical aspects of the procedure.

Figure 15A:
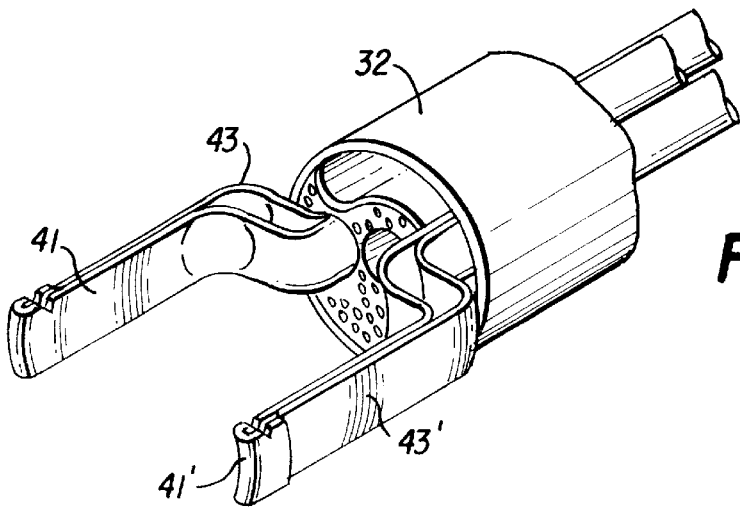
FIG. 15A illustrates a distal end of an eleventh preferred embodiment of the invention with drivers in an opened position.
Figure 15B:
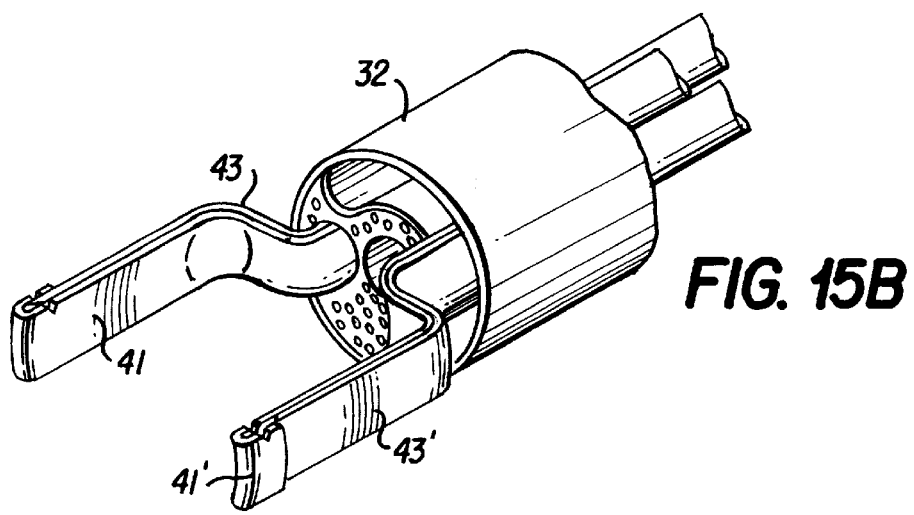
FIG. 15B illustrates a distal end of the eleventh preferred embodiment of the invention with drivers in a closed position.

FIGS. 15A and 15B illustrate an eleventh embodiment that is similar to the embodiment illustrated in FIGS. 8A and 8B. However, in this embodiment, hook members 41 open outward when in the illustrated position. Once again, the orientation and configuration of hook members 41 and 41' and keepers 43 and 43' can be varied based on the desired procedure.

Figure 16A:
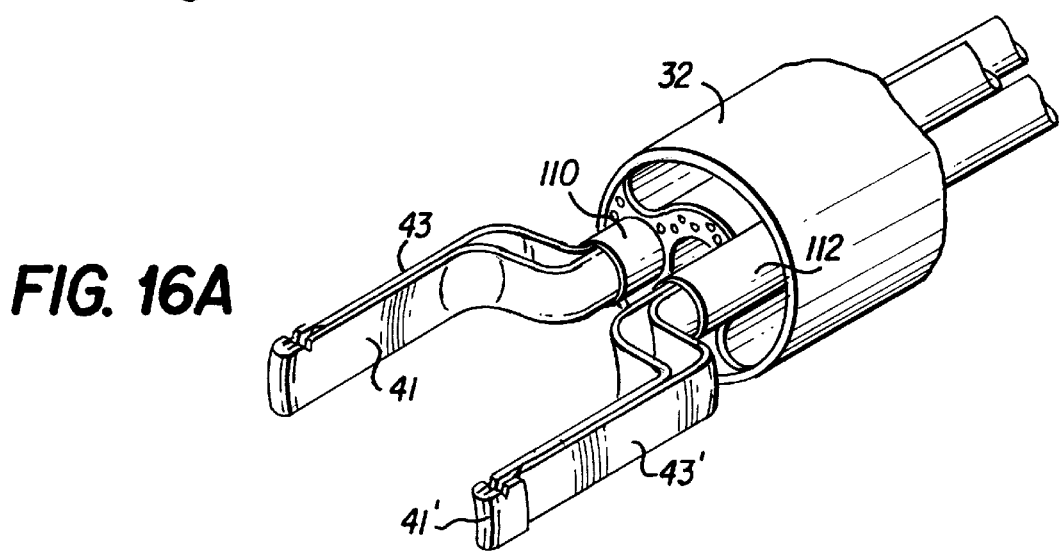
FIG. 16A illustrates a distal end of a twelfth preferred embodiment of the invention with drivers in an open position.
Figure 16B:
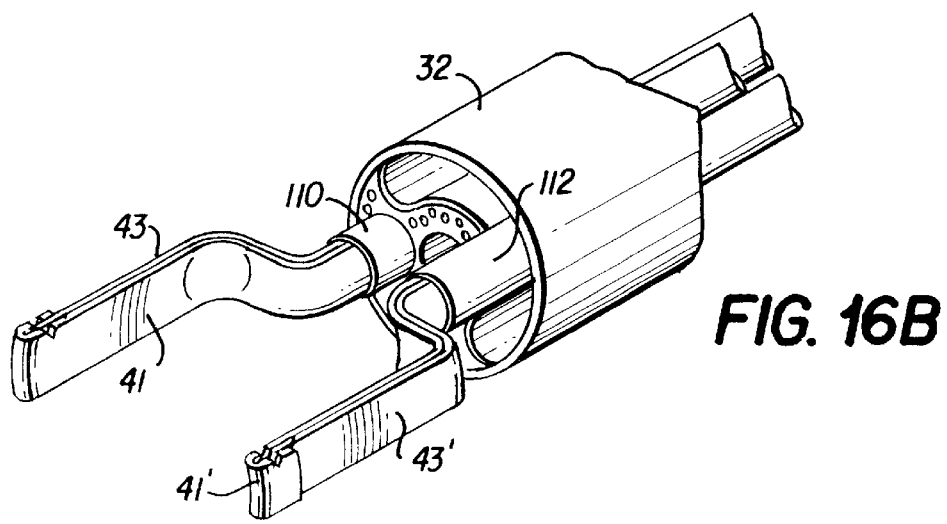
FIG. 16B illustrates a distal end of the twelfth preferred embodiment of the invention with drivers in the closed position.

FIGS. 16a and 16b illustrate a twelfth embodiment that is similar to the embodiment illustrated in FIGS. 8a and 8b and 13a and 13b. However, in this embodiment, tubular member 110 is disposed around a shaft portion of hook member 41 and keeper 43 and tubular member 112 is disposed around a shaft portion of hook member 41' and keeper 43'. Tubular members 110 and 112 define operating channels which can be used for insertion of instruments, aspiration, irrigation, or any other procedure.

Figure 17:
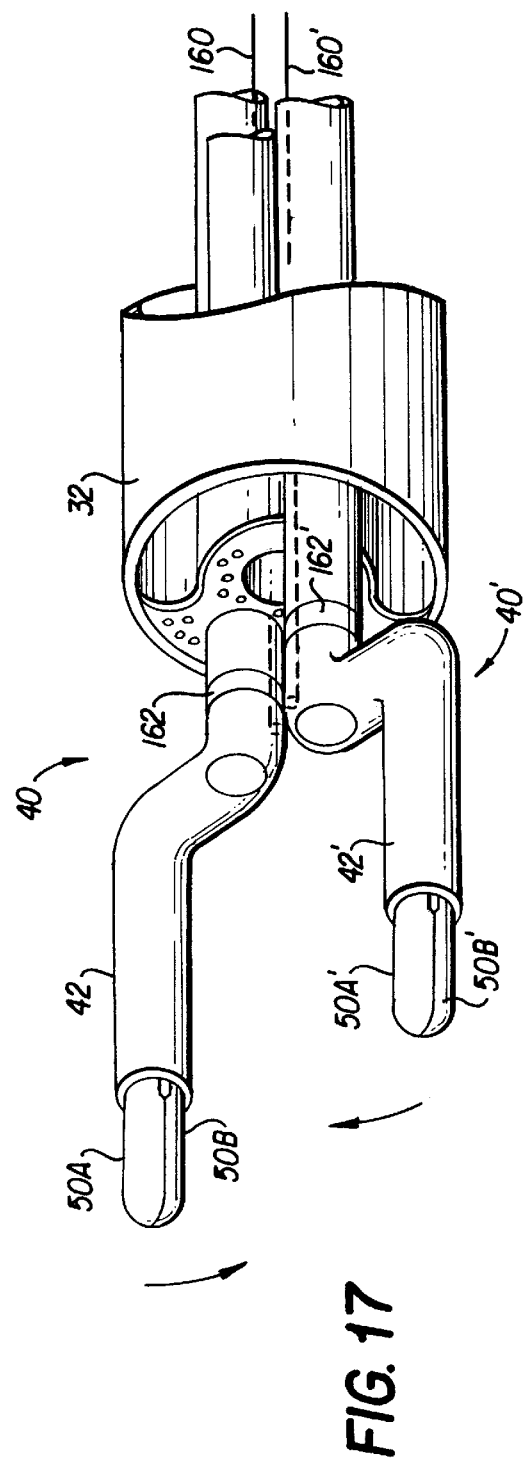
FIG. 17 illustrates a distal end of a thirteenth preferred embodiment.

FIG. 17 illustrates a thirteenth embodiment in which needle driver 40 has pivoting joint 162 and needle catcher 40' has pivoting joint 162'. The pivoting joints can be constituted of pins, flexible portions or any other pivoting configuration. Tether 160 is attached to an inner portion of needle driver 40 and tether 160' is attached to an inner portion of needle catcher 40'. Pulling the tethers from the distal end causes the associated needle holder to pivot inwards as shown by the arrows. Releasing the tethers causes the needle holders to return to the positions illustrated in FIG. 17. This motion can be used to pass a needle through tissue during a suturing procedure. Any appropriate mechanism can be used to control the pivoting motion of the needle holders. Of course, this pivoting arrangement can be used for other procedures such as lysis of adhesion.

While the needle driver and the needle catcher have been described herein as being independently controlled by separate operating mechanisms, such as push buttons and knobs slidably disposed along slots formed in the instrument, it will be appreciated that a single operating mechanism can be used to synchronize movement of the needle driver and the needle catcher relative to one another as well as operation of their respective jaws, other holding members, or other end effectors, to further simplify the procedure by allowing one-handed operation of the instrument. For example, a single operating mechanism utilizing gearing and cam arrangements can enable the user to rotate the needle catcher toward a suture needle held by the needle driver in a first direction along an arcuate path in response to a single squeeze of a handle or trigger while also causing the jaws of the needle driver to open and the jaws of the needle catcher to close so that the suture needle is transferred or passed to the needle catcher. The user can then release the handle or trigger to cause the needle catcher to rotate away from the needle driver in a second, opposite direction along the arcuate path thereby pulling the suture needle through anatomical tissue. If desired, such an operating mechanism can move the needle driver toward the needle catcher when the handle is squeezed and also move the needle driver away from the needle catcher when the handle is released. Once the needle has been pulled through the tissue, the operating mechanism can reverse the process so that, for example, if the handle is squeezed again, the operating system will cause the needle catcher to rotate toward the needle driver in the first direction along the arcuate path while also causing the jaws of the needle catcher to open and the jaws of the needle driver to close, thereby transferring the suture needle back to the needle driver for continued suturing.

In particular, handles 62 and 64 can be coupled to both needle driver 40 and needle catcher 40' in a manner which causes the desired rotation of the shafts of needle driver 40 and needle catcher 40' and the opening and closing operation of the respective jaw members necessary for a single stitch, or multiple stitches, to be effected merely by squeezing and releasing handles 62 and 64 once or multiple times. The mechanism coupling handles 62 and 64 to needle driver 40 and needle catcher 40' can be designed to accomplish any of the stitching functions disclosed above or any other appropriate motion. Such an automatic mechanism facilitates suturing by minimizing fatigue on the surgeon and reducing the possibility of operational errors.

One example of an automatic mechanism for effecting one-handed operation of suturing instrument 30 is illustrated in FIGS. 18–21. Handle 64 is fixedly connected to housing 79. Handle 62 is movable and extends through a slot in housing 79 to be mounted on shaft 120 to cause shaft 120 to rotate when handle 62 is pivoted towards handle 54. Beveled gears 122 and 124 are also mounted on shaft 120 to rotate with shaft 120. Biasing member 126, shown as a coiled spring, biases handle 62 away from handle 64 to the illustrated position.

Beveled gears 122 and 124 are coupled respectively to beveled gears 126 and 128 that are fixed on outer member 42 and outer member 42' respectively. Beveled gear 124 is coupled directly to beveled gear 126 and beveled gear 122 is coupled to beveled gear 128 through beveled gear 130. Accordingly, rotation of shaft 120 causes outer member 42 to rotate in a first direction and causes outer member 42' to rotate in a second direction opposite to the first direction. The corresponding inner members are configured to rotate with the outer members.

Projection 132 extends from inner member 44' through slots formed in outer member 42' and beveled gear 128, as is best illustrated in FIGS. 18. A free end of projection 132 slides in cam groove 136 formed in cylindrical member 170. Similarly, projection 134 extends from inner member 44 and slides in cam groove 138 formed in cylindrical member 172.

The cam grooves are shaped to cause the respective inner members to move axially, in distal and proximal directions, after the inner members rotate through a predetermined angle.

In operation, a needle is grasped in jaws of needle driver 40 in the illustrated position. When the surgeon squeezes handle 62 towards handle 64, shaft 120 rotates to cause needle driver 40 to rotate in a clockwise direction, as viewed from the distal end, and to cause needle catcher 40' to move arcuately in a counterclockwise direction, as viewed from the distal end. This results in the needle being pushed through tissue and into the jaw members of needle holder 40' at which time cam grooves 136 and 138 cause the inner members to move relative to the outer members in a manner to open jaws of needle driver 40 and close jaw members of needle catcher 40'. Releasing handles 62 and 64 permits needle holder 40 to rotate and needle catcher 40' to move arcuately in opposite directions due to the force of biasing member 125 as projections 132 and 134 continue in the same direction through cam grooves 136 and 138. Now the instrument can be compressed again to transfer the needle back to needle driver 40 for another stitch.

In some of the embodiments discussed above, two opposed jaw members are moveable toward one another. However, one of the jaw members can be fixed and the other jaw member can be moveable. Also, any appropriate proximal controls can be used to accomplish the disclosed movement. For example, any of the proximal controls disclosed in applicant's copending application Ser. No. 08/847,189, the disclosure of which is incorporated herein by reference, can be used.

The needle driver and the needle catcher, i.e. the needle holders, can be of the same design or of different designs as long as at least one is capable of grasping and releasing a needle. Also, the needle holders can be disposed in various portions of the barrel. For example, instrument 30 can have any of the configurations disclosed in the copending application Ser. No. 08/847,189. Also, either one or both of the drivers can be arcuately movable. Further, there can be more than two drivers and any of the drivers can be arcuately movable.

The jaw members can be configured to hold any type of needle or other object including, but not limited to, straight and curved needles. Further, the function of the needle driver and the needle catcher can be interchanged and suturing can be accomplished in the opposite direction depending on whether the surgeon is right-handed or left-handed. Also, one or both of the needle driver and needle catcher can be selectively or permanently fixed with respect to the barrel. Movement of the end effectors, such as the jaw members of the preferred embodiment, can be accomplished by rotating the entire barrel. Fixed needle holders are particularly suitable for open surgery in which the instrument is not inserted through a portal sleeve or the like. Of course, in place of needle holders and forceps jaws, the end effectors can be of any types, such as clip applicators, cautery electrodes with proper insulation, staplers, scissors, or the like.

One or more lengths of suture material can be attached to each suture needle at any desirable location along the body or tip of the needle including, but not limited to, the proximal end of the needle, intermediate or medial portions of the needle body, or locations adjacent the tip of the needle. It will also be appreciated that the suturing instrument according to the present invention can be used with any type of standard suturing needle including, but not limited to, needles having sharp or blunt tissue penetrating tips, and needles having tissue penetrating tips at opposite axial ends of a needle body. The arms, or connecting member, can extend transversely or of any angle with respect to the shafts.

The holding members of the needle catcher and the needle driver shown and described herein are merely exemplary of the types of needle holding mechanisms that can be used according to the present invention. Accordingly, the jaw members and other components can have any suitable configuration for cooperatively grasping needles to suture anatomical tissue including, but not limited to, configurations wherein the members pivot, slide or otherwise move relative to one another to capture and release a needle. The jaw members can, for example, be of straight, curved or angled configuration and can be provided with ribs, grooves, slots and/or holes along grasping surfaces to assure a positive grip. The jaw members can also carry cutting members, such as slots with sharp edges or protruding blades, and can have opposed arcuate or concave portions for clamping tubular objects, such as organs, without compressing the objects. Also, only one, or more than two needle holding devices can be provided in the suturing device as needed. Further, the jaws can be configured to carry a needle in a longitudinal manner during insertion of the device and the needle can be turned transversely for suturing.

Also, the "needle catcher" can be a device without jaws for merely supporting tissue during suturing. In such a case the needle driver pushes the needle through tissue while the tissue is supported at a back surface by the "needle catcher". Further, one of the needle catcher and needle driver can be fixed.

The mechanisms for moving the needle catcher and needle driver relative to one another are merely exemplary of the types of mechanisms that can be used to perform these functions and other mechanisms can be used. The particular length and curvature of the suture needles shown and described herein as well as any angular displacements of the needle driver and catcher shown and described herein are merely exemplary, and it will be appreciated that other needle lengths and angular displacements can be used. For example, the needle holders can be flexible and can be drawn into the barrel proximally to be placed in an insertion position. In the event that the end effectors are not needle holders, the appropriate controls and linkages can be provided to accomplish the desired procedure.

One of the needle holders can be used as forceps, to grasp the tissue, during suturing or can contain a clip applicator, scissors or other end effector. Therefore, the invention can be used for pickup and cutting, pickup and clipping, pickup and suturing, or lysis of adhesion procedures. Further, the suturing instrument of the invention can suture, pickup, tie and cut suture, without additional instruments. Alternatively, a forceps device can be inserted through the operating channel formed in the shaft of one of the needle holders or another operating channel. The jaw members can be used as unipolar or bipolar cautery electrodes, as a backup, by being coupled to an electrical power source by connector 109. Coagulation can be accomplished with end effectors using electric, laser, cryogenic, heat, or other forms of energy. Also, a button can be provided to switch power from one end effector to the other, button 66 for example. Tubular members 110 and 112, or any other appropriate structure, can be used to electrically insulate cautery electrodes from other parts of the instrument. Further, tissue can be clamped between adjacent needle holders or tissue can be retracted by placing adjacent needle holders between tissue portions and moving the needle holders apart.

The components of the instrument of the present invention can be made of any suitable, medical grade materials to permit sterilization for reuse or disposal for single patient use. The components can be made of multiple parts of various configurations and materials to reduce cost. The invention can have various valves, stop-cocks and seals therein to control the flow of fluid and medical devices through the suturing instrument.

The position of an endoscopic or other visualization device and the relative lengths and angles of the arms and end effectors can be adjusted to facilitate visualization. Also, the angle at which the end effectors extend from the arms can be adjustable or fixed at any value. The arms need not be perpendicular to the shafts or the end effectors and the end effectors need not be parallel to the shafts. Also, the barrel can be of any cross-sectional shape such as polygonal, elliptical, or square.

In as much as the present invention is subject to many variations, modifications and changes in detail, it is intended that all subject matter discussed above or shown in the accompanying drawings be interpreted as illustrative only and not be construed as limiting the scope of the invention which is defined by the appended claims.

What is claimed is:

1. An instrument for manipulating anatomical tissue, comprising:
    an elongated barrel having a distal end and a proximal end;
    a handle coupled to the proximal end;
    a first connecting member coupled to a distal end of said barrel;
    a first end effector extending from said first connecting member, said first end effector having a longitudinal axis that is offset from and substantially parallel to a longitudinal axis of said barrel;
    a second connecting member coupled to a distal end of said barrel, said second connecting member being coupled to said barrel to move arcuately with respect to said barrel; and
    a second end effector extending from said second connecting member, said second end effector having a longitudinal axis that is offset from a longitudinal axis of said barrel.

2. An instrument as recited in claim 1, wherein said first connecting member is rotatably coupled to said barrel.

3. An instrument as recited in claim 1, wherein said first connecting member is rotatably coupled to said barrel and said second connecting member is rotatably coupled to said barrel.

4. An instrument as recited in claim 3, wherein said first end effector comprises first needle holding members and said second end effector comprises second needle holding members.

5. An instrument as recited in claim 1, further comprising a first shaft extending through a barrel and supporting said first connecting member; and said second shaft extending through said barrel and supporting said second connecting member, said first shaft and said second shaft being substantially parallel to the longitudinal axis of said barrel.

6. An instrument as recited in claim 5, wherein said first connecting member is a first arm that extends from a distal end of said first shaft in a direction substantially perpendicular to an axis of rotation of said first shaft and said second connecting member is a second arm that extends from a distal end of said second shaft in a direction substantially perpendicular to a longitudinal axis of said second shaft.

7. An instrument as recited in claim 6 wherein each of said first arm and said second arm comprises a pair of arm members.

8. An instrument as recited in claim 4, further comprising:
    a first opening device for moving said first needle holding members toward and away from one another; and
    a second opening device for moving said second needle holding members toward and away from one another.

9. An instrument as recited in claim 6, wherein said first shaft and said second shaft are movable in proximal and distal directions.

10. An instrument as recited in claim 1, further comprising:
    a first operating channel defined in said first shaft and extending from said proximal end to said distal end.

11. An instrument as recited in claim 1, further comprising a second operating channel defined in said second shaft and extending from said proximal end to said distal end.

12. An instrument as recited in claim 9, further comprising:
    a first operating channel defined in said first shaft and extending from said proximal end to said distal end.

13. An instrument as recited in claim 9, further comprising a second operating channel defined in said second shaft and extending from said proximal end to said distal end.

14. An instrument as recited in claim 1, wherein the longitudinal axis of said first end effector is parallel to the longitudinal axis of said barrel and the longitudinal axis of said second end effector is parallel to the longitudinal axis of said barrel.

15. An instrument for manipulating anatomical tissue, comprising:
    an elongated barrel having a distal end and a proximal end;
    a handle coupled to said proximal end;
    a first connecting member extending transversely from a distal end of said barrel;
    a first end effector extending from said first connecting member, said first end effector having a longitudinal axis that is substantially parallel to a longitudinal axis of said barrel;
    a second connecting member extending transversely from a distal end of said barrel, said second connecting member being coupled to said barrel to move arcuately with respect to said barrel; and
    a second end effector extending from said second connecting member.

16. An instrument as recited in claim 15, wherein said first connecting member is rotatably coupled to said barrel.

17. An instrument as recited in claim 15, wherein said first end effector comprises first needle holding members and said second end effector comprises second needle holding members.

18. An instrument as recited in claim 15, further comprising:
    a first shaft extending through said barrel and supporting said first connecting member and a second shaft extending through said barrel and supporting said second connecting member, said first shaft and said second shaft being substantially parallel to the longitudinal axis of said barrel.

19. An instrument as recited in claim 17, further comprising
    a first opening device for moving said first needle holding members toward and away from one another; and
    a second opening device for moving said second needle holding members toward and away from one another.

20. An instrument as recited in claim 18, wherein said first shaft and said second shaft are movable in distal and proximal directions.

21. An instrument as recited in claim 18, further comprising a first operating channel defined in said first shaft and extending from a proximal end to a distal end.

22. An instrument as recited in claim 18, further comprising, a second operating channel defined in said second shaft and extending from a proximal end to a distal end.

23. An instrument as recited in claim 18, further comprising a second operating channel defined in said second shaft and extending from a proximal end to a distal end.

24. A method of suturing anatomical tissue using a length of suture material attached to a needle, said method comprising the steps of:

introducing a distal end of a barrel into an area proximate the anatomical tissue;

grasping the needle with driver needle holding members, said driver needle holding members being disposed on a driver connecting member coupled to a distal end of the barrel and having a longitudinal axis that is offset from and substantially parallel to a longitudinal axis of the barrel;

rotating the driver connecting member in a first direction to cause the needle to move in an arcuate path and to cause a tip of the needle to penetrate the anatomical tissue; and grasping the needle with a needle catcher, the needle catcher including a catcher connecting member coupled to a distal end of said barrel, and catcher needle holding members disposed on the catcher connecting member and having a longitudinal axis that is offset from a longitudinal axis of the catcher shaft, said catcher connecting member being coupled to the barrel to move arcuately with respect to the barrel.

25. A method as recited in claim 24, wherein said rotating step comprises rotating the barrel.

26. A method as recited in claim 24 further comprising the steps of:

grasping the needle with the catcher needle holding members;

releasing the needle from the driver needle holding members; and moving the catcher connecting member through the barrel in an arcuate path with respect to the barrel in a first direction to pull the needle entirely through the anatomical tissue.

27. A method as recited in claim 24, further comprising the step of moving at least one of the driver connecting member and the catcher connecting member in one of a distal direction and a proximal direction.

28. A method as recited in claim 27, further comprising the steps of:

releasing the suture needle from the driver needle holding members, rotating the driver connecting member in a second direction that is opposite to the first direction to receive a shank of the needle in the driver needle holding members;

grasping the needle in the driver needle holding members again;

releasing the needle from the catcher needle holding members; and repeating the previous steps until suturing is finished.

29. A method as recited in claim 24 wherein, during said introducing step, the driver connecting member crosses the catcher connecting member and the driver needle holding members and the catcher needle holding members are contained entirely within a diametrical dimension of said barrel.

30. A method as recited in claim 26, further comprising the steps of;

moving the barrel in an axial direction; and moving the catcher connecting member through an arcuate path in a second direction to cause the needle to penetrate the anatomical tissue again.

31. A method as recited in claim 26, further comprising the steps of:

moving the barrel away from the tissue; and moving the catcher connecting member through an arcuate path in a second direction to place the needle between the driver needle holding members.

32. A method of suturing anatomical tissue using a length of suture material attached to a needle, said method comprising the steps of:

grasping the needle with driver needle holding members, the driver needle holding members being disposed on a driver connecting member extending from a distal end of an elongate barrel;

rotating the driver connecting member in a first direction to cause a tip of the needle to penetrate the anatomical tissue;

grasping the needle with catcher needle holding members mounted on a catcher connecting member extending from a distal end of the barrel;

releasing the needle from the driver needle holding members; and moving the catcher connecting member through an arcuate path to pull the needle entirely through the anatomical tissue;

wherein all of the above steps are accomplished automatically in response to movement of a single proximal control.

33. A method as recited in claim 32, wherein the proximal control is a pair of handles that are movable toward and away from one another.

34. A method of suturing anatomical tissue using a length of suture material attached to a needle, said method comprising the steps of:

grasping the needle with a needle driver;

moving the needle driver shaft in a first direction to penetrate the anatomical tissue cause a tip of the needle to penetrate the anatomical tissue;

grasping the needle with a needle catcher;

releasing the needle from the needle driver; and moving the catcher to pull the needle entirely through the anatomical tissue;

wherein all of the above steps are accomplished automatically in response to movement of a single proximal control.

35. A method as recited in claim 34, wherein the proximal control is a pair of handles that are movable toward and away from one another.

36. An instrument for manipulating anatomical tissue comprising:

an elongated barrel having a distal end and a proximal end;

a handle coupled to said proximal end;

a first driver comprising a first shaft extending from the distal end of said barrel, a first connecting member disposed on a distal end of said first shaft, and a first end effector extending from said first connecting member, said first end effector having a longitudinal axis that is offset from and substantially parallel to a longitudinal axis of said first shaft; and a second driver comprising a second shaft extending from the distal end of said barrel, a second connecting member disposed on a distal end of said second shaft, and a second end effector extending from said second connecting member, said second end effector having a longitudinal axis that is offset from a longitudinal axis of said second shaft, said second shaft being arcuately movable through said barrel.

* * * * *